(12) United States Patent
Keum et al.

(10) Patent No.: US 12,718,371 B2
(45) Date of Patent: Aug. 25, 2026

(54) COLONOSCOPY AREA INDICATION SYSTEM AND METHOD

(71) Applicant: WAYCEN INC., Seoul (KR)

(72) Inventors: Jisoo Keum, Yongin-si (KR); Kyung Nam Kim, Suwon-si (KR)

(73) Assignee: WAYCEN INC, Seoul (KR)

( * ) Notice: Subject to any disclaimer, the term of this patent is extended or adjusted under 35 U.S.C. 154(b) by 0 days.

(21) Appl. No.: 19/258,147

(22) Filed: Jul. 2, 2025

(65) Prior Publication Data

US 2026/0127742 A1 May 7, 2026

(30) Foreign Application Priority Data

Nov. 6, 2024 (KR) ........................ 10-2024-0156341
Jan. 6, 2025 (KR) ........................ 10-2025-0001391

(51) Int. Cl.
*G06T 7/00* (2017.01)
*A61B 1/00* (2006.01)
(Continued)

(52) U.S. Cl.
CPC ...... *G06T 7/0014* (2013.01); *A61B 1/000094* (2022.02); *A61B 1/000096* (2022.02);
(Continued)

(58) Field of Classification Search
CPC ......... G06T 7/0014; G06T 2207/20132; G06T 2207/30028; G06T 2207/30096;
(Continued)

(56) References Cited

U.S. PATENT DOCUMENTS

2011/0301447 A1* 12/2011 Park ...................... G06T 7/0016 600/407
2016/0163048 A1* 6/2016 Yee ....................... A61B 6/032 382/131

(Continued)

FOREIGN PATENT DOCUMENTS

KR 10-2020-0038120 A 4/2020
WO WO-2021111756 A1 * 6/2021 ......... A61B 1/00158

OTHER PUBLICATIONS

Office Action mailed Jan. 23, 2025, issued to corresponding Korean Application No. 10-2025-0001391.

(Continued)

*Primary Examiner* — Atiba O Fitzpatrick
(74) *Attorney, Agent, or Firm* — Stein IP, LLC

(57) ABSTRACT

Proposed is a colonoscopy area indication method that includes loading a colonoscopy image analysis model and setting an analysis condition of the analysis model by a model loading/condition setting part, and initializing an analysis screen and displaying a picture of a normal colon by a controller, and preprocessing, by an image preprocessing part, a colonoscopy image received through an image receiving part so that subsequent image analysis is smoothly performed, and analyzing the preprocessed colonoscopy image by an image analysis part by using the image analysis model based on AI, and detecting and indicating, on the basis of a result of analysis by the image analysis part, at least one selected from a group of an examination area, a diverticulum area, and a lesion area in the colonoscopy image, and providing, by the controller, the result of analysis performed by the image analysis part.

16 Claims, 22 Drawing Sheets

(51) Int. Cl.
*G06V 10/25* (2022.01)
*G06V 10/26* (2022.01)
*G16H 50/20* (2018.01)
*G10L 15/08* (2006.01)

(52) U.S. Cl.
CPC .............. *G06V 10/25* (2022.01); *G06V 10/26* (2022.01); *G16H 50/20* (2018.01); *G06T 2207/20132* (2013.01); *G06T 2207/30028* (2013.01); *G06T 2207/30096* (2013.01); *G06V 2201/031* (2022.01); *G10L 15/08* (2013.01)

(58) Field of Classification Search
CPC ........ A61B 1/000094; A61B 1/000096; G06V 10/25; G06V 10/26; G06V 2201/031; G16H 50/20; G10L 15/08
See application file for complete search history.

(56) References Cited

U.S. PATENT DOCUMENTS

2021/0153808 A1* 5/2021 Tada ..................... G06T 7/0016
2021/0398655 A1* 12/2021 Evans .................. A61B 5/0836
2021/0398676 A1* 12/2021 Evans .................... G16H 15/00
2022/0020496 A1* 1/2022 Saito ..................... G06T 7/0012
2024/0233121 A1* 7/2024 Kamijo ................. G06T 7/0012
2025/0000331 A1* 1/2025 Hane ................ A61B 1/000094
2025/0095145 A1* 3/2025 Kamijo ............ A61B 1/000094

OTHER PUBLICATIONS

Notice of Allowance mailed Feb. 21, 2025, issued to corresponding Korean Application No. 10-2025-0001391.

* cited by examiner

FIG. 2A1

FIG. 2A2
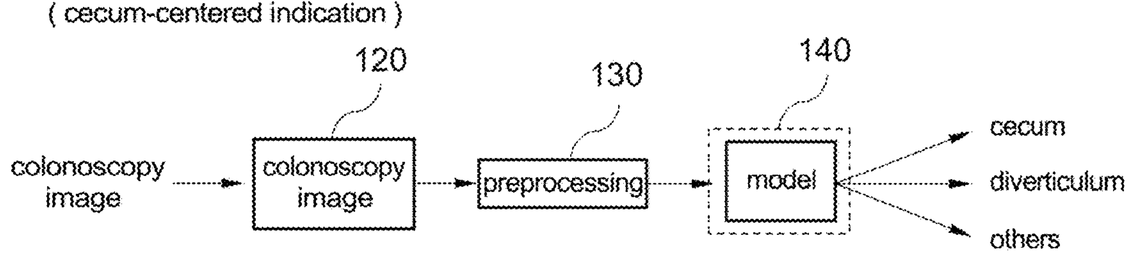
FIG. 2B1
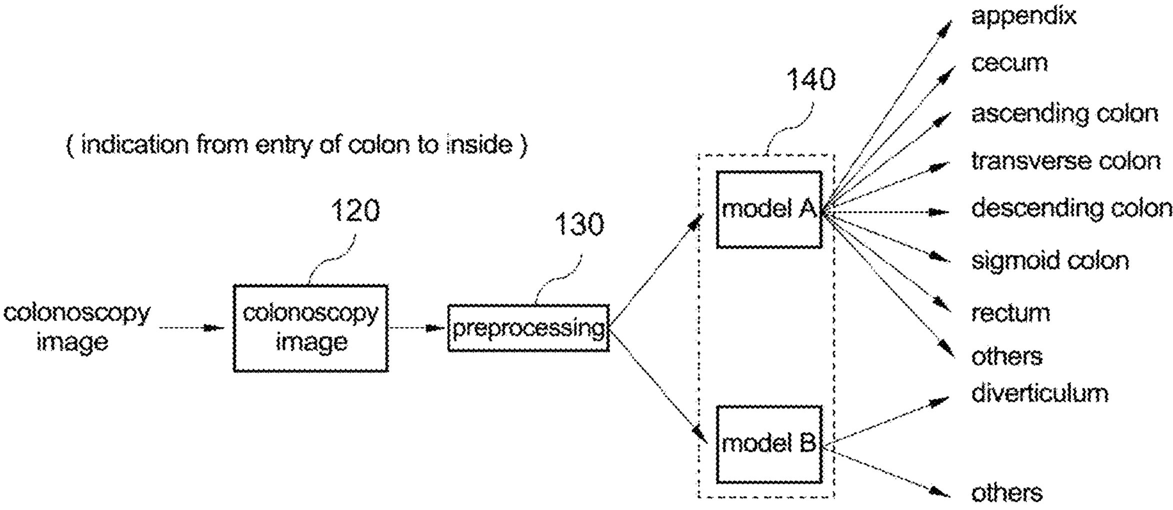
FIG. 2B2
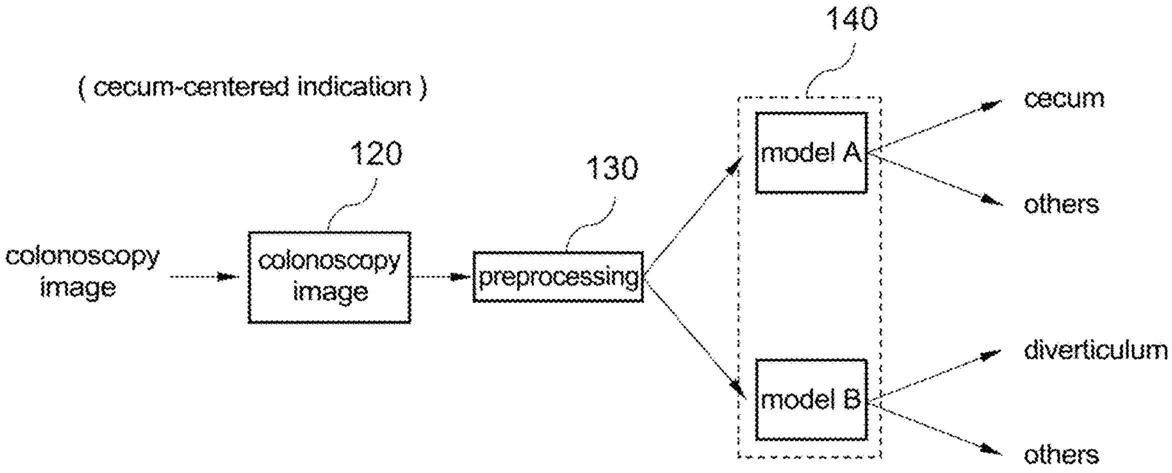

COLONOSCOPY AREA INDICATION SYSTEM AND METHOD

CROSS REFERENCE TO RELATED APPLICATION

The present application claims priority to Korean Patent Application No. 10-2024-0156341, filed Nov. 6, 2024, and Korean Patent Application No. 10-2025-0001391, filed Jan. 6, 2025, the entire contents of which are incorporated herein for all purposes by this reference.

BACKGROUND OF THE INVENTION

Field of the Invention

The present disclosure relates to a colonoscopy area indication system and method. More particularly, the present disclosure relates to a colonoscopy area indication system and method that inform an examiner of conditions, such as a diverticulum protruding from the colon wall, or indicate a diverticulum on an examination screen differently from a normal colon, in indicating a main examination area by applying an image recognition technology to a colonoscopy process.

A Korean national project supported by Korean government associated with this invention is described below.

| | |
|---|---|
| Project Unique Number | Not Assigned |
| Project Serial Number | RS-2024-00510314 |
| Government Department | Ministry of SMEs and Startups |
| Specialized Institution for Project Management | Korea Technology and Information Promotion Agency for SMEs |
| Title of Research Business | Startup Growth Technology Development (R&D) |
| Title of Project | Development of Artificial Intelligence-Based Colonoscopy Quality Enhancement Technology - Cecum Detection, Endoscopy Speed, and Examination Time Measurement Technology |
| Supervising Institute | Waycen Inc. |
| Research Period | 1 Oct. 2024-30 Sep. 2025 |

Description of the Related Art

Today, the incidence of colorectal cancer has been rapidly increasing due to the modernization of dietary habits and advancements in diagnostic technology. It is known that 80~90% of colorectal cancers begin as small polyps (adenomas) in the colon. If such polyps are detected and removed early through colonoscopy, the mortality rate from colorectal cancer can be significantly reduced.

The purpose of colorectal cancer screening is to detect colorectal cancer at an early stage in order to reduce mortality related to the colorectal cancer. According to previous studies, the effectiveness of colorectal cancer screening in reducing cancer mortality varies depending on the examination method. Cancer screening methods should have high sensitivity and specificity, no risks or complications, and low cost. Currently suggested methods for colorectal cancer screening include fecal occult blood testing, sigmoid colonoscopy, colonoscopy, and double-contrast barium enema. Fecal occult blood test has been reported to reduce colorectal cancer mortality by 15~33% in large-scale randomized clinical trials conducted in Europe. A fecal occult blood test has no complications caused by the test, is inexpensive, and is relatively simple to perform. However, it has been noted to have limitations such as low sensitivity and positive predictive value in a single test, as well as a high false-positive rate that leads to the need for additional examinations.

Therefore, screening using colonoscopy has been recommended in recent years, but it is applied in limited ways (such as additional examinations for people with abnormal results of fecal occult blood test) in national health screening programs targeting the general public due to relatively high cost, rare but serious complications (such as colon perforations), the examinee's pain and inconvenience caused by preparation, and lack of skilled endoscopists.

In the meantime, Korean Patent Application Publication No. 10-2022-0140924 discloses "DEEP-LEARNING BASED COLONOSCOPY IMAGE ANALYSIS METHOD AND IMAGE ANALYSIS SYSTEM USING THE SAME". The deep-learning based colonoscopy image analysis system includes: an endoscopy computer for receiving an image obtained by a colonoscope; a server for obtaining the image transmitted to the endoscopy computer through an application downloaded to the endoscopy computer in a hooking manner, and having a diagnosis algorithm for correcting the obtained image and performing a deep-learning based medical examination on the basis of the corrected image, and transmitting a result of diagnosis derived through the corrected image and the diagnosis algorithm to the endoscopy computer; and a display device for receiving and outputting the corrected image and the result of diagnosis from the endoscopy computer.

In the above patent document, an image is loaded and processed using a window hooking method, allowing operation without the manufacturer's application programming interface (API). In addition, an image affected by light reflection is corrected and the size of polyps is accurately measured, thereby improving the reliability of diagnosis. However, there is no separate means for informing an examiner of conditions such as diverticula during a colonoscopy process or for indicating (displaying) the conditions on an examination screen differently from a normal colon. This carries the potential risk that the examiner may cause complications such as perforations.

SUMMARY OF THE INVENTION

The present disclosure is directed to providing a colonoscopy area indication system and method that inform an examiner of conditions, such as a diverticulum protruding from the colon wall or indicate (display) a diverticulum on an examination screen differently from a normal colon, in indicating a main examination area by applying an image recognition technology to a colonoscopy process. Accordingly, the colonoscopy area indication system and method enable the examiner to conduct the examination with caution against complications, such as perforations, assist in setting a probe movement path, and allow the examiner to perform a more thorough colonoscopy.

In addition, the present disclosure is directed to providing a colonoscopy area indication system and method that indicate the main colon examination area to enable the examiner to identify the area examined so far, and report whether a cecum examination is performed to use this as an indicator of the quality of colonoscopy, and record whether there is a diverticulum so that the examiner is aware of the risk of perforations in advance when conducting a subsequent colonoscopy.

According to an embodiment of the present disclosure, there is provided a colonoscopy area indication system including:

a model loading/condition setting part configured to load a colonoscopy image analysis model, and set an analysis condition of the analysis model;

an image receiving part configured to receive a colonoscopy image frame;

an image preprocessing part configured to preprocess a colonoscopy image received through the image receiving part so that subsequent image analysis is smoothly performed;

an image analysis part configured to analyze the colonoscopy image preprocessed by the image preprocessing part by using the image analysis model based on artificial intelligence (AI), and detect and indicate, on the basis of a result of analysis, at least one selected from a group of an examination area, a diverticulum area, and a lesion area in the colonoscopy image; and a controller configured to check states and control operations of the model loading/condition setting part, the image receiving part, the image preprocessing part, and the image analysis part, and initialize an analysis screen and display a picture of a normal colon when the model loading/condition setting part completes loading of the colonoscopy image analysis model and setting of the analysis condition of the analysis model, and provide the result of analysis performed by the image analysis part.

Herein, preprocessing of the colonoscopy image by the image preprocessing part may include analysis region cropping and input size adjustment.

In addition, the image analysis model of the image analysis part may be configured as a single image analysis model for detecting the examination area and the diverticulum area.

In addition, the image analysis model of the image analysis part may be configured to include an examination area detection model for detecting the examination area, and a diverticulum detection model for detecting the diverticulum area.

In addition, the image analysis model of the image analysis part may be configured to include an examination area detection model for detecting the examination area, a diverticulum detection model for detecting the diverticulum area, and a lesion detection model for detecting the lesion area.

Herein, the lesion detection model may have a lesion attribute identification function for determining whether a lesion is benign or malignant.

In addition, the image analysis model of the image analysis part may be configured to include a cecum/diverticulum detection model for detecting a cecum and a diverticulum, and a lesion detection model for detecting the lesion area.

Herein, the lesion detection model may have a lesion attribute identification function for determining whether a lesion is benign or malignant.

In addition, in detecting and indicating at least one selected from the group of the examination area, the diverticulum area, and the lesion area in the colonoscopy image by the image analysis part, the examination area may include an appendix, a cecum, an ascending colon, a transverse colon, a descending colon, a sigmoid colon, and a rectum.

In addition, in detecting and indicating at least one selected from the group of the examination area, the diverticulum area, and the lesion area in the colonoscopy image by the image analysis part, the controller may be configured to transmit, to the image analysis part, an indication condition change command to indicate a cecum in a case of an appendix, and differently indicate a diverticulum in the picture of the normal colon.

In addition, in detecting and indicating at least one selected from the group of the examination area, the diverticulum area, and the lesion area in the colonoscopy image by the image analysis part, the controller may be configured to transmit, to the image analysis part, an indication condition change command to not indicate a diverticulum in the picture of the normal colon or to report a colonic diverticulum, and to indicate examination time and withdrawal time.

In addition, according to an embodiment of the present disclosure, there is provided a colonoscopy area indication method including:

a) loading, by a model loading/condition setting part, a colonoscopy image analysis model and setting an analysis condition of the analysis model;

b) initializing, by a controller, an analysis screen and displaying a picture of a normal colon;

c) preprocessing, by an image preprocessing part, a colonoscopy image received through an image receiving part so that subsequent image analysis is smoothly performed;

d) analyzing, by an image analysis part, the preprocessed colonoscopy image using the image analysis model based on AI;

e) detecting and indicating, on the basis of a result of analysis by the image analysis part, at least one selected from a group of an examination area, a diverticulum area, and a lesion area in the colonoscopy image; and f) providing, by the controller, the result of analysis performed by the image analysis part.

Herein, in the step c), preprocessing of the colonoscopy image by the image preprocessing part may include analysis region cropping and input size adjustment.

In addition, in the step d), the image analysis model may be configured as a single image analysis model for detecting the examination area and the diverticulum area.

In addition, in the step d), the image analysis model may be configured to include an examination area detection model for detecting the examination area, and a diverticulum detection model for detecting the diverticulum area.

In addition, in the step d), the image analysis model may be configured to include an examination area detection model for detecting the examination area, a diverticulum detection model for detecting the diverticulum area, and a lesion detection model for detecting the lesion area.

Herein, the lesion detection model may have a lesion attribute identification function for determining whether a lesion is benign or malignant.

In addition, in the step d), the image analysis model may be configured to include a cecum/diverticulum detection model for detecting a cecum and a diverticulum, and a lesion detection model for detecting the lesion area.

Herein, the lesion detection model may have a lesion attribute identification function for determining whether a lesion is benign or malignant.

In addition, in the step e), in detecting and indicating at least one selected from the group of the examination area, the diverticulum area, and the lesion area in the colonoscopy image by the image analysis part, the examination area may include an appendix, a cecum, an ascending colon, a transverse colon, a descending colon, a sigmoid colon, and a rectum.

In addition, in the step e), in detecting and indicating at least one selected from the group of the examination area, the diverticulum area, and the lesion area in the colonoscopy image by the image analysis part, the controller may be configured to transmit, to the image analysis part, an indication condition change command to indicate a cecum in a case of an appendix, and differently indicate a diverticulum in the picture of the normal colon.

In addition, in the step e), in detecting and indicating at least one selected from the group of the examination area, the diverticulum area, and the lesion area in the colonoscopy image by the image analysis part, the controller may be configured to transmit, to the image analysis part, an indication condition change command to not indicate a diverticulum in the picture of the normal colon or to report a colonic diverticulum, and to indicate examination time and withdrawal time.

In addition, according to another embodiment of the present disclosure, there is provided a colonoscopy area indication system including:

a model loading/condition setting part configured to load a colonoscopy image analysis model and a speech keyword recognition model, and set an analysis condition of the analysis model;

an image receiving part configured to receive a colonoscopy image frame;

an image preprocessing part configured to preprocess a colonoscopy image received through the image receiving part so that subsequent image analysis is smoothly performed;

an image analysis part configured to analyze the colonoscopy image preprocessed by the image preprocessing part by using the image analysis model based on artificial intelligence (AI), and detect and indicate, on the basis of a result of analysis, at least one selected from a group of an examination area, a diverticulum area, and a lesion area in the colonoscopy image;

a speech recognition part configured to read audio from a buffer storing the audio while the image analysis part performs the image analysis, and analyze the audio using the speech keyword recognition model based on AI, and recognize a speech keyword on the basis of the result of analysis and transmit the speech keyword to the image analysis part; and a controller configured to check states and control operations of the model loading/condition setting part, the image receiving part, the image preprocessing part, the image analysis part, and the speech recognition part, and initialize an analysis screen and display a picture of a normal colon when the model loading/condition setting part completes loading of the colonoscopy image analysis model and setting of the analysis condition of the analysis model, and provide the result of analysis performed by the image analysis part, wherein the result of analysis is provided by linking an analysis target detected by the image analysis model with a speech command (keyword) related to the analysis target spoken by an examiner.

Herein, preprocessing of the colonoscopy image by the image preprocessing part may include analysis region cropping and input size adjustment.

In addition, the image analysis model of the image analysis part may be configured as a single image analysis model for detecting the examination area and the diverticulum area.

In addition, the image analysis model of the image analysis part may be configured to include an examination area detection model for detecting the examination area, and a diverticulum detection model for detecting the diverticulum area.

In addition, the image analysis model of the image analysis part may be configured to include an examination area detection model for detecting the examination area, a diverticulum detection model for detecting the diverticulum area, and a lesion detection model for detecting the lesion area.

Herein, the lesion detection model may have a lesion attribute identification function for determining whether a lesion is benign or malignant.

In addition, the image analysis model of the image analysis part may be configured to include a cecum/diverticulum detection model for detecting a cecum and a diverticulum, and a lesion detection model for detecting the lesion area.

Herein, the lesion detection model may have a lesion attribute identification function for determining whether a lesion is benign or malignant.

In addition, in detecting and indicating at least one selected from the group of the examination area, the diverticulum area, and the lesion area in the colonoscopy image by the image analysis part, the examination area may include an appendix, a cecum, an ascending colon, a transverse colon, a descending colon, a sigmoid colon, and a rectum.

In addition, in detecting and indicating at least one selected from the group of the examination area, the diverticulum area, and the lesion area in the colonoscopy image by the image analysis part, the controller may be configured to transmit, to the image analysis part, an indication condition change command to indicate a cecum in a case of an appendix, and differently indicate a diverticulum in the picture of the normal colon.

In addition, in detecting and indicating at least one selected from the group of the examination area, the diverticulum area, and the lesion area in the colonoscopy image by the image analysis part, the controller may be configured to transmit, to the image analysis part, an indication condition change command to not indicate a diverticulum in the picture of the normal colon or to report a colonic diverticulum, and to indicate examination time and withdrawal time.

In addition, according to another embodiment of the present disclosure, there is provided a colonoscopy area indication method including:

p) loading, by a model loading/condition setting part, a colonoscopy image analysis model and a speech keyword recognition model and setting an analysis condition of the analysis model;

q) initializing, by a controller, an analysis screen and displaying a picture of a normal colon;

r) preprocessing, by an image preprocessing part, a colonoscopy image received through an image receiving part so that subsequent image analysis is smoothly performed;

s) analyzing, by an image analysis part, the colonoscopy image preprocessed by the image preprocessing part using the image analysis model based on AI;

t) detecting and indicating, on the basis of a result of analysis by the image analysis part, at least one selected from a group of an examination area, a diverticulum area, and a lesion area in the colonoscopy image;

u) reading, by a speech recognition part, audio from a buffer storing the audio while the image analysis part performs the image analysis and analyzing the audio using the speech keyword recognition model based on AI, and recognizing a speech keyword on the basis of the result of analysis and transmitting the speech keyword to the image analysis part; and v) providing, by the controller, the result of analysis by linking an analysis target detected by the image analysis model of the image analysis part with a speech command (keyword) related to the analysis target spoken by an examiner.

Herein, in the step r), preprocessing of the colonoscopy image by the image preprocessing part may include analysis region cropping and input size adjustment.

In addition, in the step s), the image analysis model may be configured as a single image analysis model for detecting the examination area and the diverticulum area.

In addition, in the step s), the image analysis model may be configured to include an examination area detection model for detecting the examination area, and a diverticulum detection model for detecting the diverticulum area.

In addition, in the step s), the image analysis model may be configured to include an examination area detection model for detecting the examination area, a diverticulum detection model for detecting the diverticulum area, and a lesion detection model for detecting the lesion area.

Herein, the lesion detection model may have a lesion attribute identification function for determining whether a lesion is benign or malignant.

In addition, in the step s), the image analysis model may be configured to include a cecum/diverticulum detection model for detecting a cecum and a diverticulum, and a lesion detection model for detecting the lesion area.

Herein, the lesion detection model may have a lesion attribute identification function for determining whether a lesion is benign or malignant.

In addition, in the step t), in detecting and indicating at least one selected from the group of the examination area, the diverticulum area, and the lesion area in the colonoscopy image by the image analysis part, the examination area may include an appendix, a cecum, an ascending colon, a transverse colon, a descending colon, a sigmoid colon, and a rectum.

In addition, in the step t), in detecting and indicating at least one selected from the group of the examination area, the diverticulum area, and the lesion area in the colonoscopy image by the image analysis part, the controller may be configured to transmit, to the image analysis part, an indication condition change command to indicate a cecum in a case of an appendix, and differently indicate a diverticulum in the picture of the normal colon.

In addition, in the step t), in detecting and indicating at least one selected from the group of the examination area, the diverticulum area, and the lesion area in the colonoscopy image by the image analysis part, the controller may be configured to transmit, to the image analysis part, an indication condition change command to not indicate a diverticulum in the picture of the normal colon or to report a colonic diverticulum, and to indicate examination time and withdrawal time.

According to the present disclosure, the colonoscopy area indication system and method can inform the examiner of conditions, such as a diverticulum protruding from the colon wall, or can indicate (display) a diverticulum on the examination screen differently from a normal colon, in indicating the main examination area by applying the image recognition technology to the colonoscopy process. Accordingly, the colonoscopy area indication system and method enable the examiner to conduct the examination with caution against complications, such as perforations, assist in setting a probe movement path, and allow the examiner to perform a more thorough colonoscopy.

In addition, the colonoscopy area indication system and method indicate the main colon examination area to enable the examiner to identify the area examined so far, and report whether a cecum examination is performed to use this as an indicator of the quality of colonoscopy, and record whether there is a diverticulum so that the examiner is aware of the risk of perforations in advance when conducting a subsequent colonoscopy.

BRIEF DESCRIPTION OF THE DRAWINGS

The above and other objectives, features, and other advantages of the present disclosure will be more clearly understood from the following detailed description when taken in conjunction with the accompanying drawings, in which:

FIGS. 2A1, 2A2, 2B1, 2B2, 2C, and 2D are diagrams illustrating examples of configurations of an image analysis model;

DETAILED DESCRIPTION OF THE INVENTION

Hereinafter, an embodiment of the present disclosure will be described with reference to the accompanying drawings.

Figure 1:
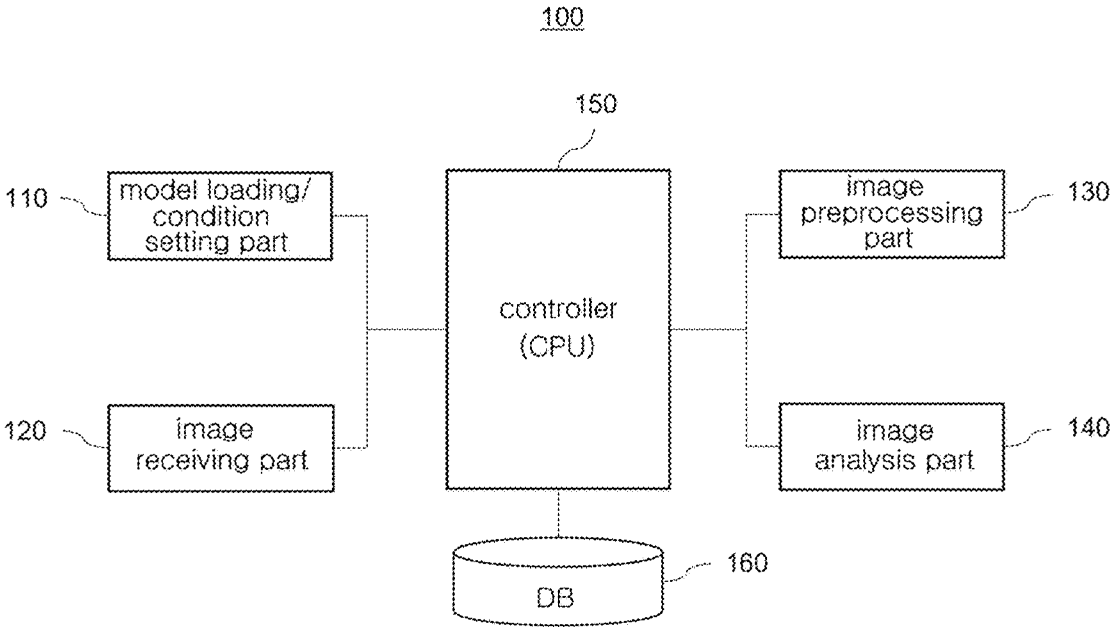
FIG. 1 is a diagram schematically illustrating the configuration of a colonoscopy area indication system according to an embodiment of the present disclosure.
Figure 1:
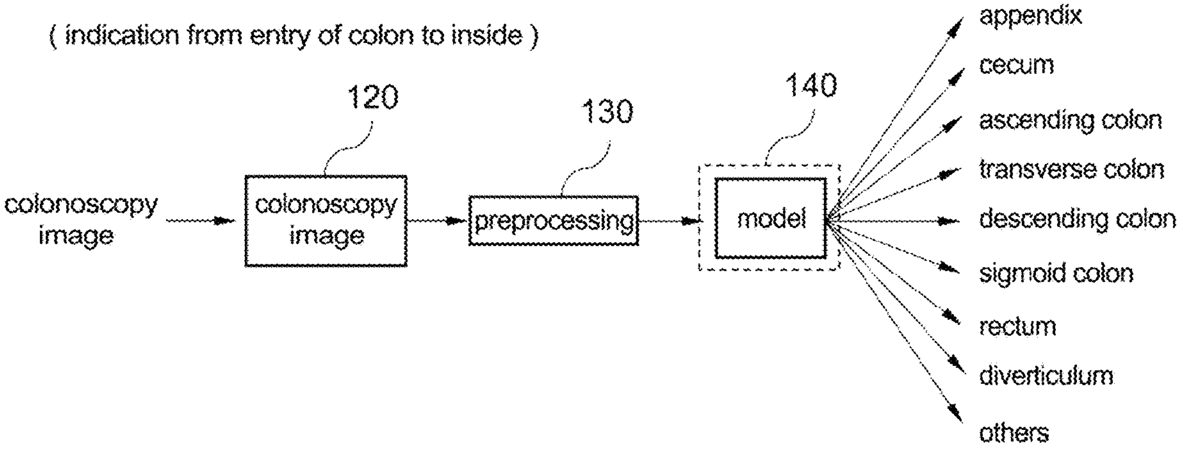

FIG. 1 is a diagram schematically illustrating the configuration of a colonoscopy area indication system according to an embodiment of the present disclosure.

Referring to FIG. 1, a colonoscopy area indication system 100 according to an embodiment of the present disclosure may include a model loading/condition setting part 110, an image receiving part 120, an image preprocessing part 130, an image analysis part 140, and a controller 150.

The model loading/condition setting part 110 loads a colonoscopy image analysis model and sets an analysis condition of the analysis model. Herein, the analysis condition of the analysis model may be set, for example, to a predicted probability value of 0.85 or higher.

The image receiving part 120 receives a colonoscopy image frame.

The image preprocessing part 130 preprocesses a colonoscopy image received through the image receiving part 120 so that subsequent image analysis is smoothly performed. Herein, the preprocessing of the colonoscopy image by the image preprocessing part 130 as described above may include analysis region cropping and input size adjustment.

The image analysis part 140 analyzes the colonoscopy image preprocessed by the image preprocessing part 130 by using the image analysis model based on artificial intelligence (AI), and detects and indicates, on the basis of a result of analysis, at least one selected from the group of an examination area, a diverticulum area, and a lesion area in the colonoscopy image. Herein, the image analysis model of the image analysis part 140 may be configured as a single image analysis model for detecting an examination area and a diverticulum area as shown in FIGS. 2A1 and 2A2. In FIGS. 2A1 and 2A2, FIG. 2A1 shows an example of indication from the entry of the colon to the inside of the colon, and FIG. 2A2 shows an example of cecum-centered indication.

In addition, as shown in FIGS. 2B1, 2B2, the image analysis model of the image analysis part 140 may include an examination area detection model (model A) for detecting an examination area, and a diverticulum detection model (model B) for detecting a diverticulum area. In FIGS. 2B1, 2B2, FIG. 2B1 shows an example of indication from the entry of the colon to the inside of the colon, and FIG. 2B2 shows an example of cecum-centered indication.

Figure 2C:
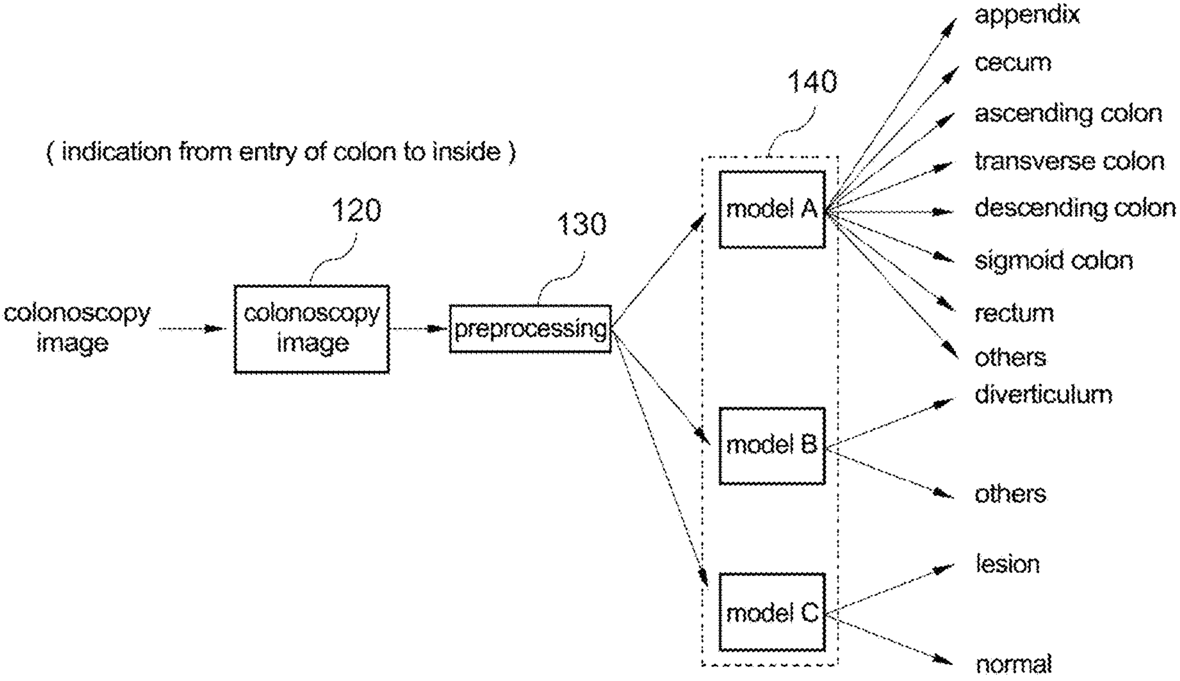

In addition, as shown in FIG. 2C, the image analysis model of the image analysis part 140 may include an examination area detection model (model A) for detecting an examination area, a diverticulum detection model (model B) for detecting a diverticulum area, and a lesion detection model (model C) for detecting a lesion area. Herein, the lesion detection model (model C) may include a lesion attribute identification function for determining whether the lesion is benign or malignant.

Figure 2D:
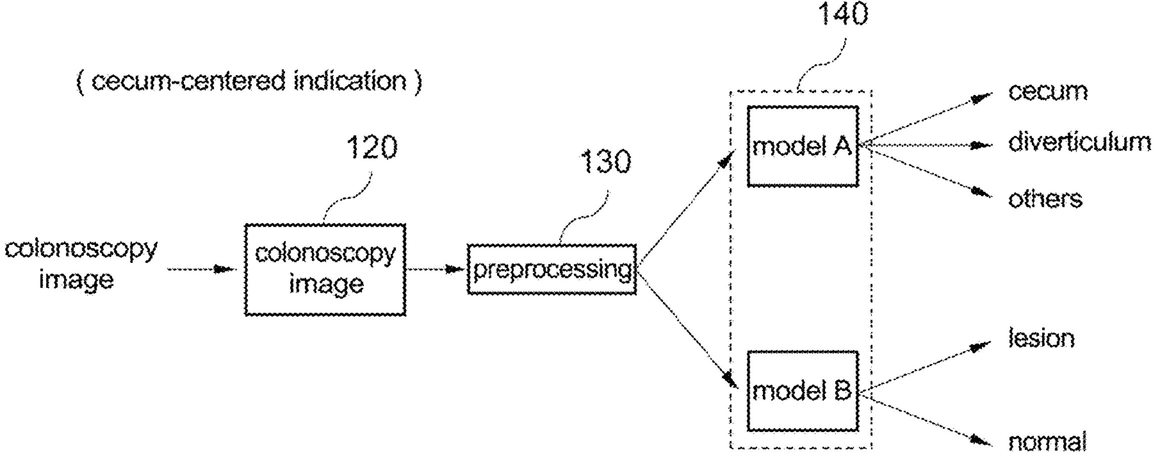

In addition, as shown in FIG. 2D, the image analysis model of the image analysis part 140 may include a cecum/diverticulum detection model (model A) for detecting the cecum and a diverticulum, and a lesion detection model (model B) for detecting a lesion area. Herein, the lesion detection model (model B) may include a lesion attribute identification function for determining whether the lesion is benign or malignant.

In addition, in detecting and indicating at least one selected from the group of an examination area, a diverticulum area, and a lesion area in the colonoscopy image by the image analysis part 140, the examination area may include the appendix, cecum, ascending colon, transverse colon, descending colon, sigmoid colon, and rectum, as shown in FIGS. 2A1, 2A2 to 2C.

The controller 150 checks the states and controls the operations of the model loading/condition setting part 110, the image receiving part 120, the image preprocessing part 130, and the image analysis part 140. When the model loading/condition setting part 110 completes the loading of the colonoscopy image analysis model and the setting of the analysis condition of the analysis model, the controller initializes an analysis screen, displays a picture of a normal colon, and provides a result of analysis performed by the image analysis part 140. Herein, in detecting and indicating at least one selected from the group of an examination area, a diverticulum area, and a lesion area in the colonoscopy image by the image analysis part 140, the controller 150 may transmit, to the image analysis part 140, an indication condition change command to indicate the cecum in the case of the appendix and differently indicate the diverticulum in the picture of the normal colon.

In addition, in detecting and indicating at least one selected from the group of an examination area, a diverticulum area, and a lesion area in the colonoscopy image by the image analysis part 140, the controller 150 may transmit, to the image analysis part 140, an indication condition change command to not indicate the diverticulum in the picture of the normal colon or to report a colonic diverticulum (for example, the alarm or the indication of the region), and to indicate the examination time and the withdrawal time.

In FIG. 1, reference numeral 160 denotes a database (DB). The database (DB) 160 stores and manages various software programs for system operation, as well as data or information required when the model loading/condition setting part 110, the image receiving part 120, the image preprocessing part 130, and the image analysis part 140 perform functions or process tasks related to model loading and condition setting, image preprocessing, and image analysis, and data on a result of colonoscopy image analysis performed by the image analysis model.

Herein, the model loading/condition setting part 110, the image receiving part 120, the image preprocessing part 130, the image analysis part 140, the controller 150, and the database (DB) 160 may be integrated as a whole and configured as a single computer system.

Hereinafter, a colonoscopy area indication method based on a colonoscopy area indication system having the configuration as described above according to an embodiment of the present disclosure will be described.

Figure 3:
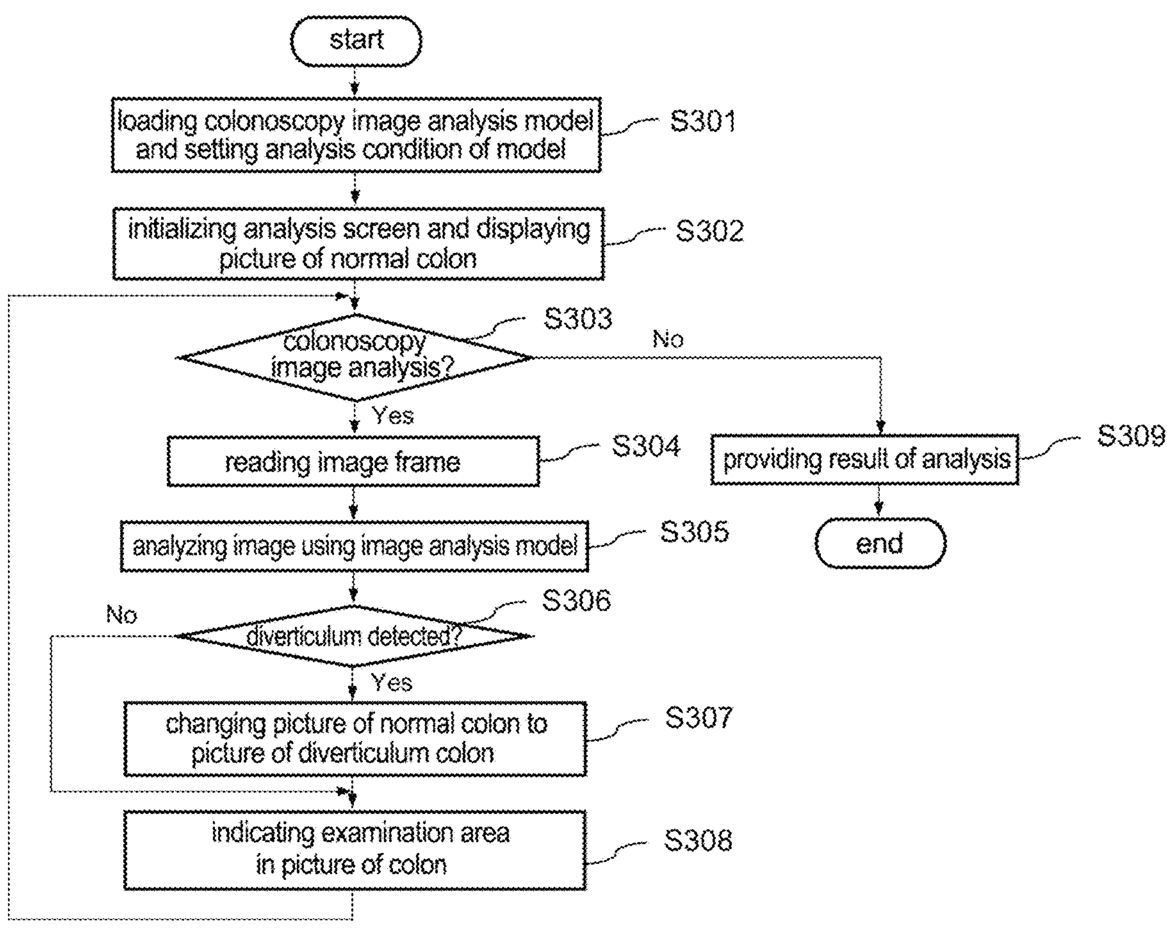
FIG. 3 is a flowchart illustrating a process of performing a colonoscopy area indication method according to an embodiment of the present disclosure.

FIG. 3 is a flowchart illustrating a process of performing a colonoscopy area indication method according to an embodiment of the present disclosure.

Referring to FIG. 3, in a colonoscopy area indication method according to an embodiment of the present disclosure, first, the model loading/condition setting part 110 loads a colonoscopy image analysis model, and sets an analysis condition (for example, a predicted probability value of 0.85 or higher) of the analysis model in step S301.

Then, the controller 150 initializes an analysis screen and displays a picture of a normal colon in step S302.

As described above, after the loading of the model and the setting of the analysis condition are completed, the analysis screen is initialized and the picture of the normal colon is displayed, and then the controller 150 determines whether to perform colonoscopy image analysis in step S303. When colonoscopy image analysis is required as determined, the image preprocessing part 130 reads a colonoscopy image (image frame) received through the image receiving part 120, and preprocesses the colonoscopy image so that subsequent image analysis is smoothly performed in step S304. Herein, the preprocessing of the colonoscopy image by the image preprocessing part 130 may include analysis region cropping and input size adjustment.

When the preprocessing of the colonoscopy image is completed in this manner, the image analysis part 140 analyzes the preprocessed colonoscopy image using the image analysis model based on AI in step S305. Herein, the image analysis model may be configured as a single image analysis model for detecting an examination area and a diverticulum area, as shown in FIGS. 2A1, 2A2 as described above. In addition, as shown in FIGS. 2B1, 2B2, the image analysis model may include an examination area detection model (model A) for detecting an examination area, and a diverticulum detection model (model B) for detecting a diverticulum area. In addition, as shown in FIG. 2C, the image analysis model may include an examination area detection model (model A) for detecting an examination area, a diverticulum detection model (model B) for detecting a diverticulum area, and a lesion detection model (model C) for detecting a lesion area. Herein, the lesion detection model (model C) may include a lesion attribute identification function for determining whether the lesion is benign or malignant. In addition, as shown in FIG. 2D, the image analysis model may include a cecum/diverticulum detection model (model A) for detecting the cecum and a diverticulum, and a lesion detection model (model B) for detecting a lesion area. Herein, the lesion detection model (model B) may include a lesion attribute identification function for determining whether the lesion is benign or malignant.

In addition, the image analysis part 140 detects and indicates, on the basis of a result of analysis, at least one selected from the group of an examination area, a diverticulum area, and a lesion area in the colonoscopy image in steps S306 to S308. Herein, in detecting and indicating at least one selected from the group of an examination area, a diverticulum area, and a lesion area in the colonoscopy image by the image analysis part 140, the examination area may include the appendix, cecum, ascending colon, transverse colon, descending colon, sigmoid colon, and rectum.

Herein, steps S306 to S308 will be described in more detail.

When the colonoscopy image analysis is completed by the image analysis part 140 in step S305, the controller 150 determines whether a diverticulum is detected in step S306. When a diverticulum is detected, the controller changes the picture of the normal colon to a picture of a diverticulum colon and displays the picture of the diverticulum colon (see FIGS. 13 to 16) in step S307, and indicates the examination area in the picture of the colon in step S308.

Afterward, when no further colonoscopy image analysis is required as determined in step S303, the controller 150 provides a result of the most recently performed analysis by the image analysis part 140 in step S309.

Figure 4:
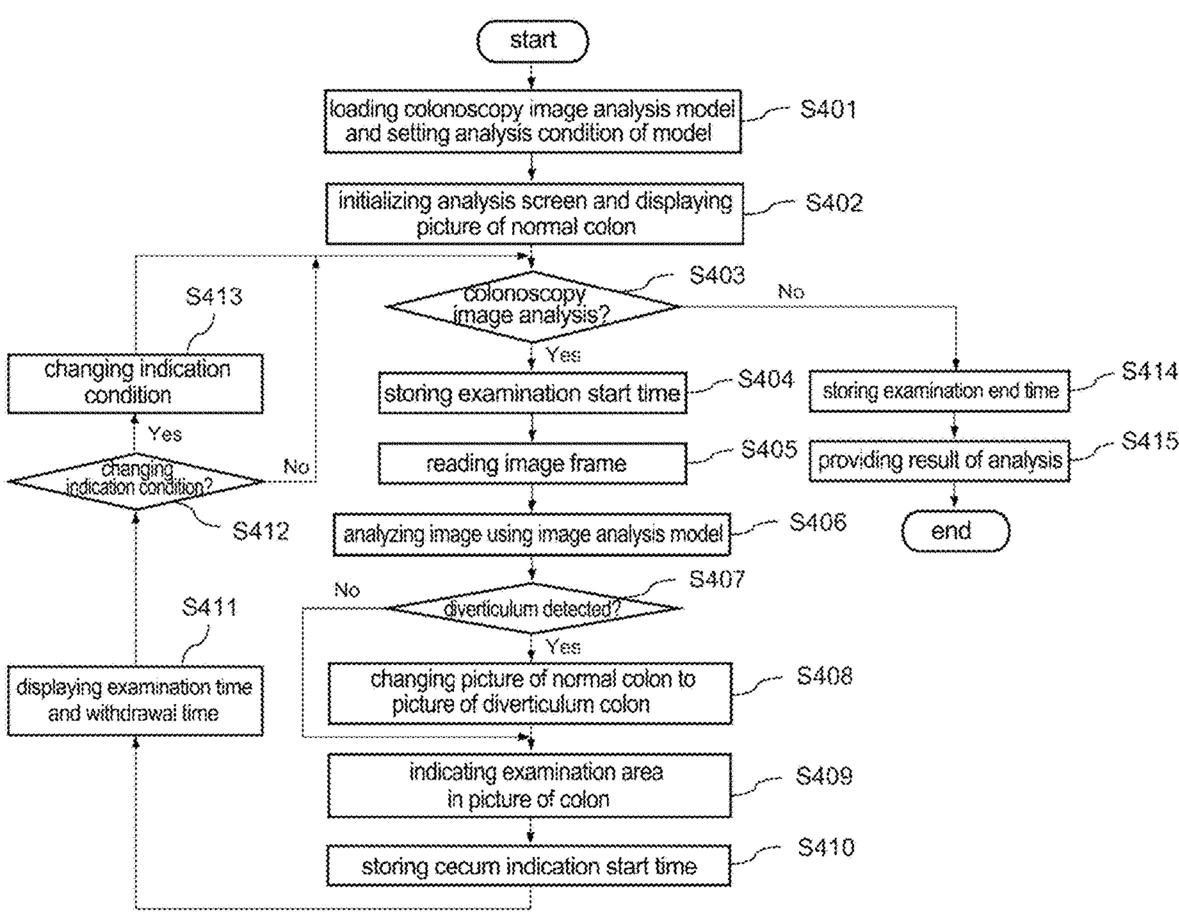
FIG. 4 is a flowchart illustrating a process of performing a first variation of the colonoscopy area indication method of FIG. 3.

In the meantime, FIG. 4 is a flowchart illustrating a process of performing a first variation of the colonoscopy area indication method of FIG. 3.

Referring to FIG. 4, the process is identical to that of FIG. 3 described above except that the process of FIG. 4 further includes storing the examination start time in step S404, storing the cecum indication start time in step S410, displaying the examination time and the withdrawal time in step S411, determining whether to change an indication condition in step S412, changing the indication condition in step S413, and storing the examination end time in step S414. Therefore, the description of the portions (steps S401 to S403, S405 to S409, and S415) that are identical to those in FIG. 3 will be replaced by the description of the portions (that is, steps S301 to S303, S304 to S308, and S309) of FIG. 3, and only the portions different from FIG. 3 will be described.

When colonoscopy image analysis is required as determined in step S403 of FIG. 4, the controller 150 stores the examination start time in the database 160 in step S404.

Afterward, as described above with reference to FIG. 3, the image preprocessing part 130 reads a colonoscopy image (image frame) received through the image receiving part 120, and preprocesses the colonoscopy image so that subsequent image analysis is smoothly performed in step S405.

In addition, the controller 150 indicates the examination area in the picture of the colon in step S409, and stores the cecum indication start time in step S410. Afterward, the controller 150 displays the examination time and the withdrawal time in step S411. Herein, the examination time refers to the time from the examination start time to the current (examination end) time, and the withdrawal time refers to the time from the cecum indication start time to the current (examination end) time.

In addition, the controller 150 determines whether to change the indication condition in step S412, and changes the indication condition when the changing of the indication condition is required in step S413. Herein, the controller 150 may transmit, to the image analysis part 140, an indication condition change command to indicate the cecum in the case of the appendix and differently indicate the diverticulum in the picture of the normal colon.

In addition, the controller 150 may transmit, to the image analysis part 140, an indication condition change command to not indicate the diverticulum in the picture of the normal colon or to report a colonic diverticulum (for example, the alarm or the indication of the region), and to indicate the examination time and the withdrawal time.

In the meantime, when no further colonoscopy image analysis is required as determined in step S403, the controller 150 stores the examination end time in step S414, and provides a result of analysis up to the current (examination end) time in step S415.

Figure 5:
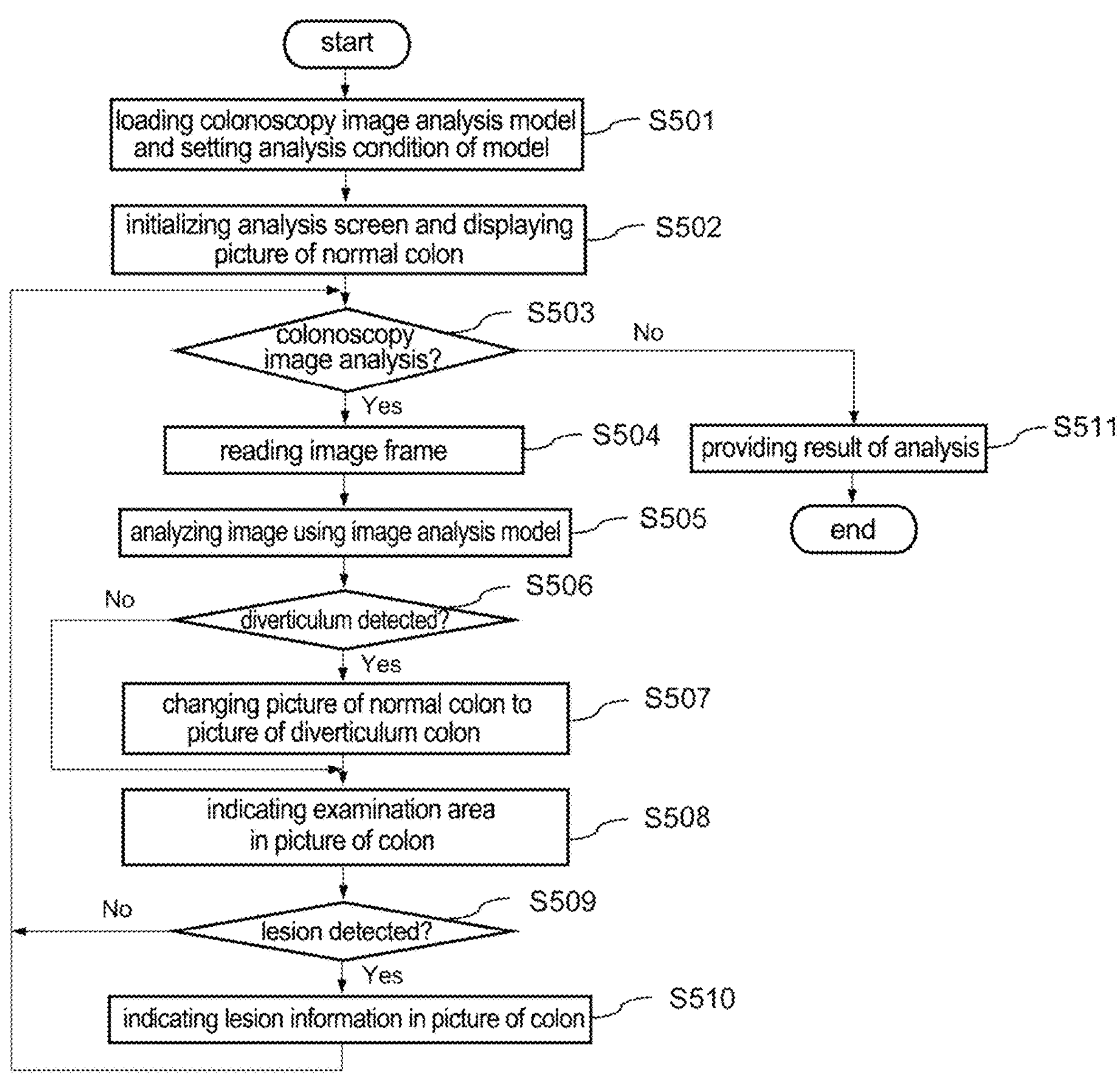
FIG. 5 is a flowchart illustrating a process of performing a second variation of the colonoscopy area indication method of FIG. 3.

FIG. 5 is a flowchart illustrating a process of performing a second variation of the colonoscopy area indication method of FIG. 3.

Referring to FIG. 5, the process is identical to that of FIG. 3 described above except that the process of FIG. 5 further includes determining whether a lesion is detected in step S509, and indicating lesion information in the picture of the colon in step S510. Therefore, the description of the portions that are identical to those in FIG. 3 will be replaced by the description of the portions of FIG. 3, and only the portions different from FIG. 3 will be described.

In FIG. 5, the controller 150 indicates the examination area in the picture of the colon picture in step S508, and determines whether a lesion is detected in step S509, and indicates lesion information in the picture of the colon when the lesion is detected in step S510.

Figure 6:
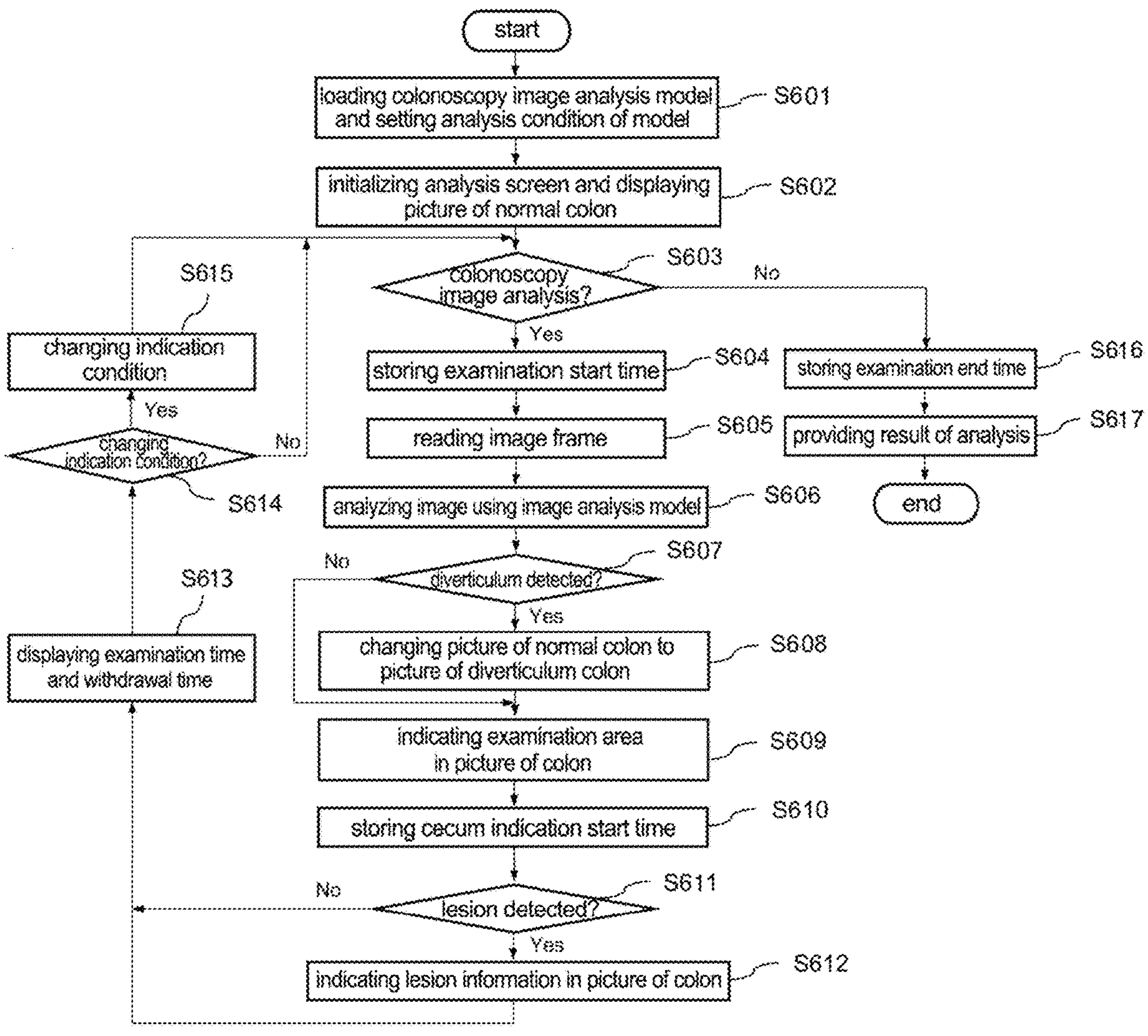
FIG. 6 is a flowchart illustrating a process of performing a third variation of the colonoscopy area indication method of FIG. 3.

FIG. 6 is a flowchart illustrating a process of performing a third variation of the colonoscopy area indication method of FIG. 3.

Referring to FIG. 6, the process is identical to that of FIG. 4 described above except that the process of FIG. 6 further includes determining whether a lesion is detected in step S611, and indicating lesion information in the picture of the colon in step S612.

That is, when colonoscopy image analysis is required as determined in step S603 of FIG. 6, the controller 150 stores the examination start time in the database 160 in step S604.

Afterward, as described above with reference to FIG. 3, the image preprocessing part 130 reads a colonoscopy image (image frame) received through the image receiving part 120, and preprocesses the colonoscopy image so that subsequent image analysis is smoothly performed in step S605.

In addition, the controller 150 indicates the examination area in the picture of the colon in step S609, and stores the cecum indication start time in step S610. Afterward, the controller 150 determines whether a lesion is detected in step S611, and indicates lesion information in the picture of the colon when the lesion is detected in step S612.

Next, the controller 150 displays the examination time and the withdrawal time in step S613. Herein, the examination time refers to the time from the examination start time to the current (examination end) time, and the withdrawal time refers to the time from the cecum indication start time to the current (examination end) time.

In addition, the controller 150 determines whether to change the indication condition in step S614, and changes the indication condition when the changing of the indication condition is required in step S615. Herein, the controller 150 may transmit, to the image analysis part 140, an indication condition change command to indicate the cecum in the case of the appendix and differently indicate the diverticulum in the picture of the normal colon.

In addition, the controller 150 may transmit, to the image analysis part 140, an indication condition change command to not indicate the diverticulum in the picture of the normal colon or to report a colonic diverticulum (for example, the alarm or the indication of the region), and to indicate the examination time and the withdrawal time.

In the meantime, when no further colonoscopy image analysis is required as determined in step S603, the controller 150 stores the examination end time in step S616, and provides a result of analysis up to the current (examination end) time in step S617.

Figure 7:
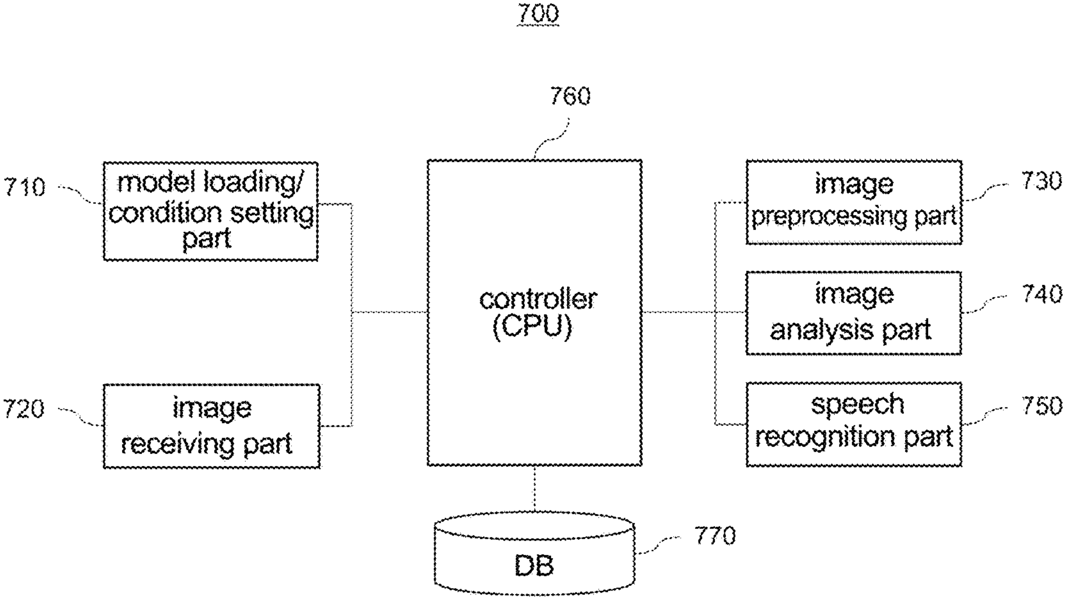
FIG. 7 is a diagram schematically illustrating the configuration of a colonoscopy area indication system according to another embodiment of the present disclosure.

FIG. 7 is a diagram schematically illustrating the configuration of a colonoscopy area indication system according to another embodiment of the present disclosure.

Referring to FIG. 7, a colonoscopy area indication system 700 according to another embodiment of the present disclosure includes, fundamentally, the same elements as the colonoscopy area indication system 100 according to an embodiment described above with reference to FIG. 1. However, there is a difference in that the colonoscopy area indication system 700 according to the embodiment further includes a speech recognition part 750.

As shown in FIG. 7, a colonoscopy area indication system 700 according to another embodiment of the present disclosure may include a model loading/condition setting part 710, an image receiving part 720, an image preprocessing part 730, an image analysis part 740, a speech recognition part 750, and a controller 760.

The model loading/condition setting part 710 loads a colonoscopy image analysis model and sets an analysis condition of the analysis model. Herein, the analysis condition of the analysis model may be set, for example, to a predicted probability value of 0.85 or higher.

The image receiving part 720 receives a colonoscopy image frame.

The image preprocessing part 730 preprocesses a colonoscopy image received through the image receiving part 720 so that subsequent image analysis is smoothly performed. Herein, the preprocessing of the colonoscopy image by the image preprocessing part 730 as described above may include analysis region cropping and input size adjustment.

The image analysis part 740 analyzes the colonoscopy image preprocessed by the image preprocessing part 730 by using the image analysis model based on artificial intelligence (AI), and detects and indicates, on the basis of a result of analysis, at least one selected from the group of an examination area, a diverticulum area, and a lesion area in the colonoscopy image. Herein, the image analysis model of the image analysis part 740 may be configured as a single image analysis model for detecting an examination area and a diverticulum area as shown in FIGS. 2A1, 2A2. In FIGS. 2A1, 2A2, FIG. 2A1 shows an example of indication from the entry of the colon to the inside of the colon, and FIG. 2A2 shows an example of cecum-centered indication.

In addition, as shown in FIGS. 2B1, 2B2, the image analysis model of the image analysis part 740 may include an examination area detection model (model A) for detecting an examination area, and a diverticulum detection model (model B) for detecting a diverticulum area. In FIGS. 2B1, 2B2, FIG. 2B1 shows an example of indication from the entry of the colon to the inside of the colon, and FIG. 2B2 shows an example of cecum-centered indication.

In addition, as shown in FIG. 2C, the image analysis model of the image analysis part 740 may include an examination area detection model (model A) for detecting an examination area, a diverticulum detection model (model B) for detecting a diverticulum area, and a lesion detection model (model C) for detecting a lesion area. Herein, the lesion detection model (model C) may include a lesion attribute identification function for determining whether the lesion is benign or malignant.

In addition, as shown in FIG. 2D, the image analysis model of the image analysis part 740 may include a cecum/diverticulum detection model (model A) for detecting the cecum and a diverticulum, and a lesion detection model (model B) for detecting a lesion area. Herein, the lesion detection model (model B) may include a lesion attribute identification function for determining whether the lesion is benign or malignant.

In addition, in detecting and indicating at least one selected from the group of an examination area, a diverticulum area, and a lesion area in the colonoscopy image by the image analysis part 740, the examination area may include the appendix, cecum, ascending colon, transverse colon, descending colon, sigmoid colon, and rectum.

The speech recognition part 750 reads audio from a buffer (located in an internal memory of the speech recognition part 750), which stores audio, while the image analysis part 740 performs image analysis, and analyzes the audio using an AI-based speech keyword recognition model, and recognizes a speech keyword on the basis of a result of analysis and transmits the speech keyword to the image analysis part 740.

The controller 760 checks the states and controls the operations of the model loading/condition setting part 710, the image receiving part 720, the image preprocessing part 730, the image analysis part 740, and the speech recognition part 750. When the model loading/condition setting part 710 completes the loading of the colonoscopy image analysis model and the setting of the analysis condition of the analysis model, the controller initializes an analysis screen, displays a picture of a normal colon, and provides a result of analysis performed by the image analysis part 740. The controller provides the result of analysis by linking an analysis target detected by the image analysis model with a speech command (keyword) related to the analysis target spoken by an examiner.

Herein, in detecting and indicating at least one selected from the group of an examination area, a diverticulum area, and a lesion area in the colonoscopy image by the image analysis part 740, the controller 760 may transmit, to the image analysis part 740, an indication condition change command to indicate the cecum in the case of the appendix and differently indicate the diverticulum in the picture of the normal colon.

In addition, in detecting and indicating at least one selected from the group of an examination area, a diverticulum area, and a lesion area in the colonoscopy image by the image analysis part 740, the controller 760 may transmit, to the image analysis part 740, an indication condition change command to not indicate the diverticulum in the picture of the normal colon or to report a colonic diverticulum (for example, the alarm or the indication of the region), and to indicate the examination time and the withdrawal time.

In FIG. 7, reference numeral 770 denotes a database (DB). The database (DB) 770 stores and manages various software programs for system operation, as well as data or information required when the model loading/condition setting part 710, the image receiving part 720, the image preprocessing part 730, the image analysis part 740, and the speech recognition part 750 perform functions or process tasks related to model loading and condition setting, image preprocessing, image analysis, and speech recognition, and data on a result of colonoscopy image analysis performed by the image analysis model.

Herein, the model loading/condition setting part 710, the image receiving part 720, the image preprocessing part 730, the image analysis part 740, the speech recognition part 750, the controller 760, and the database (DB) 770 may be integrated as a whole and configured as a single computer system.

Hereinafter, a colonoscopy area indication method based on a colonoscopy area indication system having the configuration as described above according to another embodiment of the present disclosure will be described.

Figure 8:
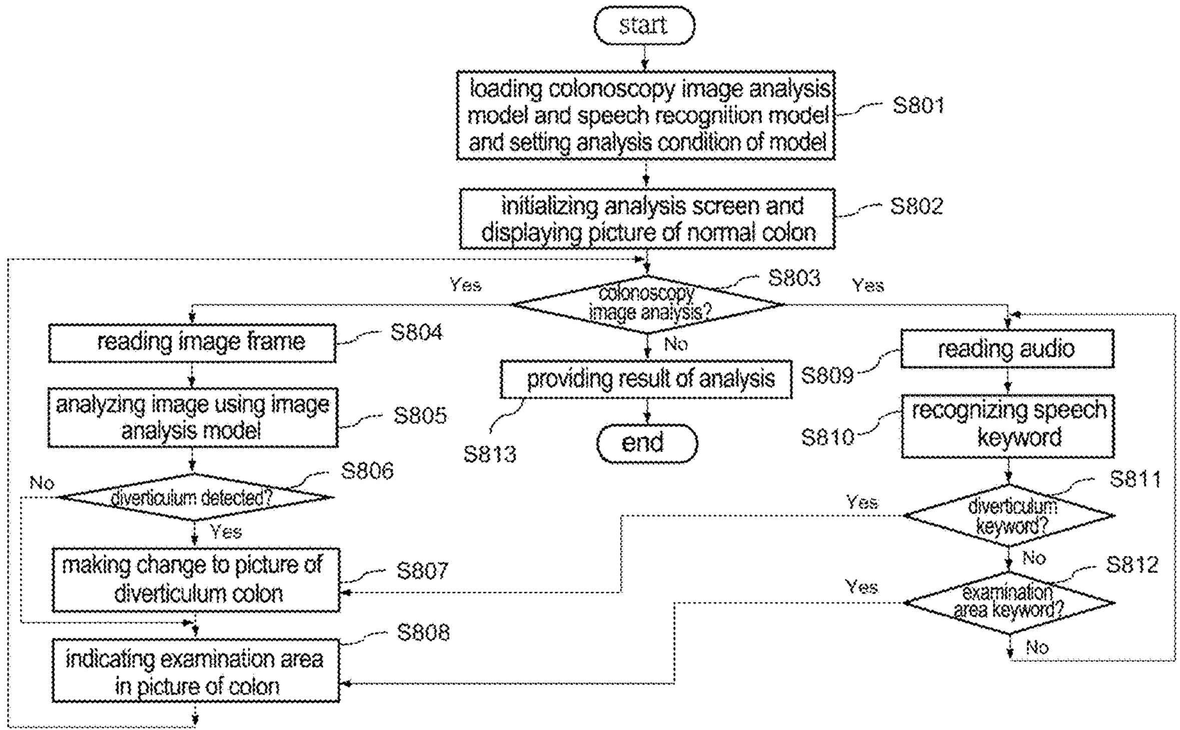
FIG. 8 is a flowchart illustrating a process of performing a colonoscopy area indication method according to another embodiment of the present disclosure.

FIG. 8 is a flowchart illustrating a process of performing a colonoscopy area indication method according to another embodiment of the present disclosure.

Referring to FIG. 8, in a colonoscopy area indication method according to another embodiment of the present disclosure, first, the model loading/condition setting part 710 loads a colonoscopy image analysis model and a speech recognition model, and sets an analysis condition (for example, a predicted probability value of 0.85 or higher) of the analysis model in step S801.

Then, the controller 760 initializes an analysis screen and displays a picture of a normal colon in step S802.

As described above, after the loading of the colonoscopy image analysis model, the loading of the speech recognition model, and the setting of the analysis condition of the model are completed, the analysis screen is initialized and the picture of the normal colon is displayed, and then the controller 760 determines whether to perform colonoscopy image analysis in step S803. When colonoscopy image analysis is required as determined, the image preprocessing part 730 reads a colonoscopy image (image frame) received through the image receiving part 720, and preprocesses the colonoscopy image so that subsequent image analysis is smoothly performed in step S804. Herein, the preprocessing of the colonoscopy image by the image preprocessing part 730 may include analysis region cropping and input size adjustment.

When the preprocessing of the colonoscopy image is completed in this manner, the image analysis part 740 analyzes the preprocessed colonoscopy image using the image analysis model based on AI in step S805. Herein, the image analysis model may be configured as a single image analysis model for detecting an examination area and a diverticulum area, as shown in FIGS. 2A1, 2A2 as described above. In addition, as shown in FIGS. 2B1, 2B2, the image analysis model may include an examination area detection model (model A) for detecting an examination area, and a diverticulum detection model (model B) for detecting a diverticulum area. In addition, as shown in FIG. 2C, the image analysis model may include an examination area detection model (model A) for detecting an examination area, a diverticulum detection model (model B) for detecting a diverticulum area, and a lesion detection model (model C) for detecting a lesion area. Herein, the lesion detection model (model C) may include a lesion attribute identification function for determining whether the lesion is benign or malignant. In addition, as shown in FIG. 2D, the image analysis model may include a cecum/diverticulum detection model (model A) for detecting the cecum and a diverticulum, and a lesion detection model (model B) for detecting a lesion area. Herein, the lesion detection model (model B) may include a lesion attribute identification function for determining whether the lesion is benign or malignant.

In addition, the image analysis part 740 detects and indicates, on the basis of a result of analysis, at least one selected from the group of an examination area, a diverticulum area, and a lesion area in the colonoscopy image in steps S806 to S808. Herein, in detecting and indicating at least one selected from the group of an examination area, a diverticulum area, and a lesion area in the colonoscopy image by the image analysis part 740, the examination area may include the appendix, cecum, ascending colon, transverse colon, descending colon, sigmoid colon, and rectum.

Herein, steps S806 to S808 will be described in more detail.

When the colonoscopy image analysis is completed by the image analysis part 740 in step S805, the controller 760 determines whether a diverticulum is detected in step S806. When a diverticulum is detected, the controller changes the picture of the normal colon to a picture of a diverticulum colon and displays the picture of the diverticulum colon (see FIGS. 13 to 16) in step S807, and indicates the examination area in the picture of the colon in step S808.

In the meantime, when colonoscopy image analysis is required as determined in step S803, the speech recognition part 750 reads audio from the buffer storing audio while the image analysis part 740 performs image analysis, and analyzes the audio using the AI-based speech keyword recognition model in step S809, and recognizes a speech keyword on the basis of a result of analysis in step S810, and transmits the speech keyword to the image analysis part 740.

That is, the speech recognition part 750 recognizes the speech keyword and determines whether the speech keyword is a diverticulum keyword in step S811. When the speech keyword is the diverticulum keyword, proceeding to step S807 takes place to change the speech keyword into a diverticulum colon picture.

In addition, when the speech keyword is not the diverticulum keyword as determined above, the speech recognition part 750 determines whether the speech keyword is an examination area keyword in step S812. When the speech keyword is the examination area keyword, proceeding to step S808 takes place to indicate the examination area in the picture of the colon.

Afterward, when no further colonoscopy image analysis is required as determined in step S803, the controller 760 links the analysis target detected by the image analysis model of the image analysis part 740 with the speech command (keyword) related to the analysis target spoken by an examiner, and provides a result of analysis performed up to the current (examination end) time by the image analysis part 740 in step S813.

Figure 9:
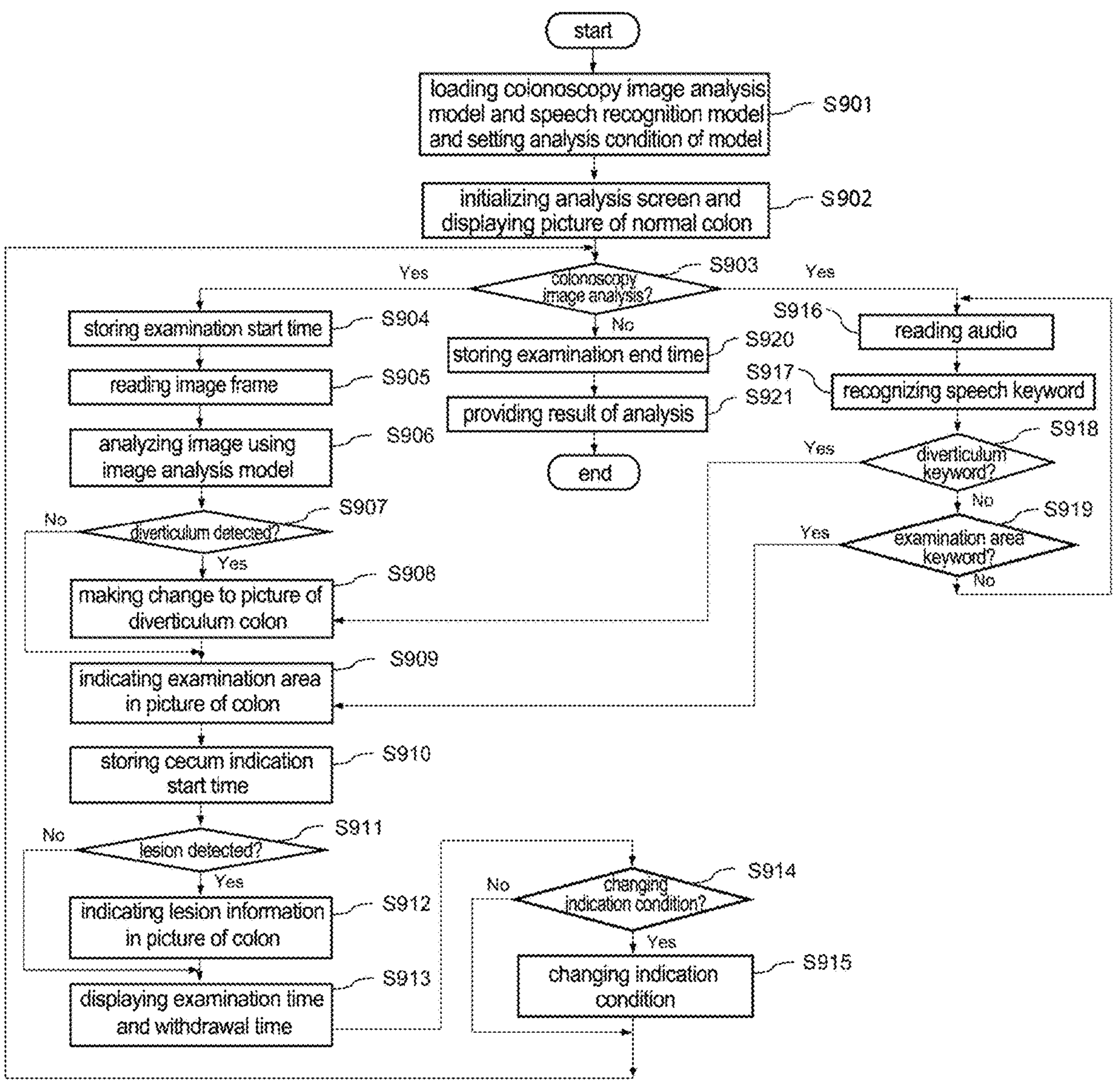
FIG. 9 is a flowchart illustrating a process of performing a variation of a colonoscopy area indication method according to another embodiment of the present disclosure.

FIG. 9 is a flowchart illustrating a process of performing a variation of a colonoscopy area indication method according to another embodiment of the present disclosure.

Referring to FIG. 9, the process is identical to that of FIG. 8 described above except that the process of FIG. 9 further includes storing the examination start time in step S904, storing the cecum indication start time in step S910, determining whether a lesion is detected in step S911, indicating lesion information in the picture of the colon in step S912, displaying the examination time and the withdrawal time in step S913, determining whether to change the indication condition in step S914, changing the indication condition in step S915, storing the examination end time in step S920. Therefore, the description of the portions that are identical to those in FIG. 8 will be replaced by the description of the portions of FIG. 8, and only the portions different from FIG. 8 will be described.

When colonoscopy image analysis is required as determined in step S903 of FIG. 9, the controller 760 stores the examination start time in the database 770 in step S904.

Afterward, as described above with reference to FIG. 8, the image preprocessing part 730 reads a colonoscopy image (image frame) received through the image receiving part 720, and preprocesses the colonoscopy image so that subsequent image analysis is smoothly performed in step S905.

In addition, the controller 760 indicates the examination area in the picture of the colon in step S909, and stores the cecum indication start time in step S910. Afterward, the controller 760 determines whether a lesion is detected in step S911, and indicates lesion information in the picture of the colon when the lesion is detected in step S912.

Next, the controller 760 displays the examination time and the withdrawal time in step S913. Herein, the examination time refers to the time from the examination start time to the current (examination end) time, and the withdrawal time refers to the time from the cecum indication start time to the current (examination end) time.

In addition, the controller 760 determines whether to change the indication condition in step S914, and changes the indication condition when the changing of the indication condition is required in step S915. Herein, the controller 760 may transmit, to the image analysis part 740, an indication condition change command to indicate the cecum in the case of the appendix and differently indicate the diverticulum in the picture of the normal colon.

In addition, the controller 760 may transmit, to the image analysis part 740, an indication condition change command to not indicate the diverticulum in the picture of the normal colon or to report a colonic diverticulum (for example, the alarm or the indication of the region), and to indicate the examination time and the withdrawal time.

In the meantime, when no further colonoscopy image analysis is required as determined in step S903, the controller 760 stores the examination end time in step S920, and provides a result of analysis up to the current (examination end) time in step S921.

Hereinafter, additional description will be provided regarding the colonoscopy area indication system and method according to the present disclosure as described above.

Figure 10A:
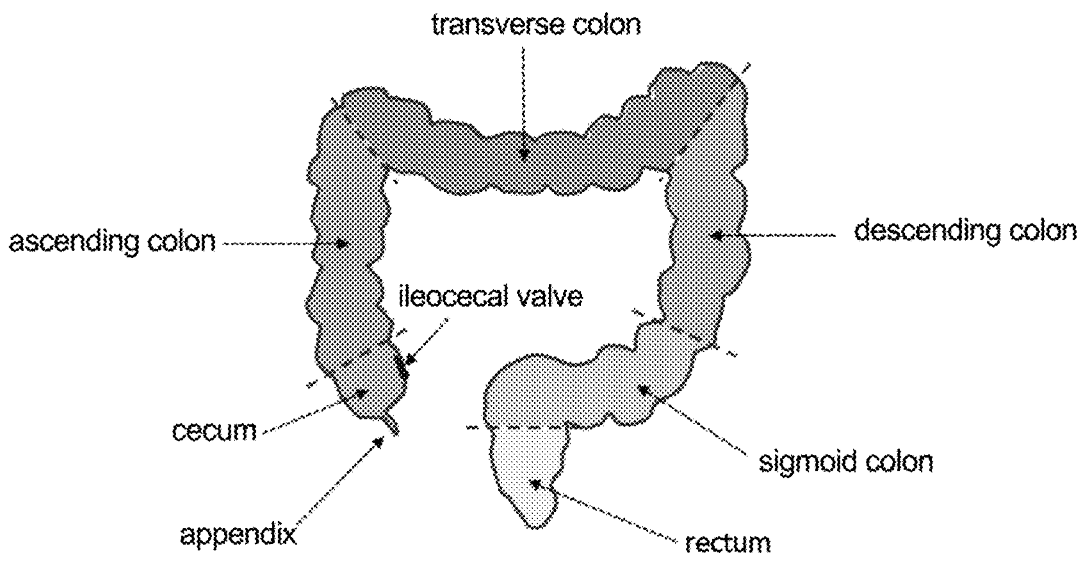
FIGS. 10A, 10B, and 10C are diagrams illustrating a main area of the colon.
Figure 10B:
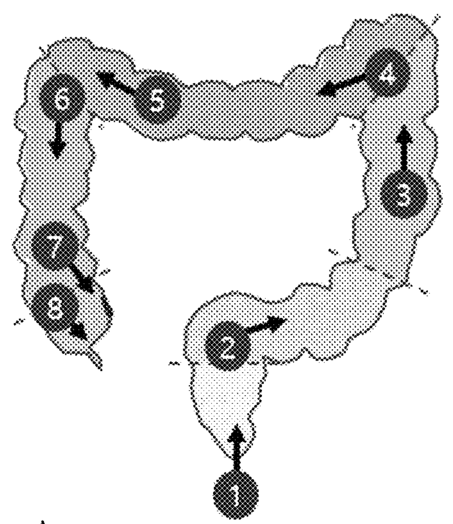
Figure 10C:
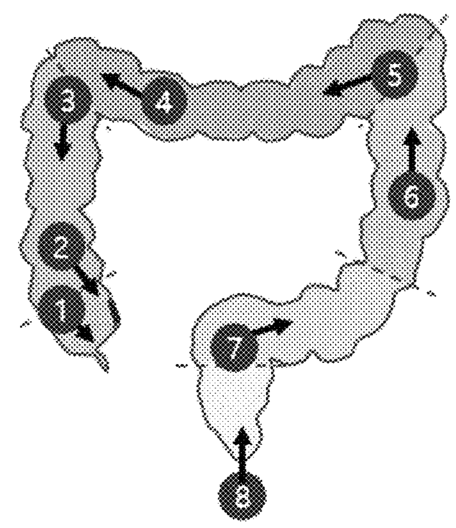

FIGS. 10A, 10B, and 10C are diagrams illustrating a main area of the colon.

Referring to FIGS. 10A, 10B, and 10C, FIG. 10A shows the main area of the colon, FIG. 10B shows the examination sequence (colonoscopy picture capture direction) during a probe insertion process, and FIG. 10C shows the examination sequence during a probe withdrawal process.

Referring to FIGS. 10A and 10B, the colonoscope is inserted through the rectum and into the colon. The colonoscope inserted into the colon captures the inside of the colon in the following order: the sigmoid colon→the descending colon→the transverse colon→the ascending colon→the cecum→the appendix.

Referring to FIGS. 10A and 10C, this is an examination during the probe withdrawal process. The colonoscope is inserted to the distal end of the colon, and is withdrawn and captures, in reverse order, the inside of the colon in the following order: the appendix→the cecum→the ascending colon→the transverse colon→the descending colon→the sigmoid colon→the rectum. In FIG. 10A, the ileocecal valve represents the junction of the cecum and the small intestine.

In the series of colonoscope probe movement and image capturing as described above, in the examination during the probe insertion process in FIG. 10B, it is considered that the cecum is checked when the probe is inserted up to position 8. After checking the cecum, the examination is performed while the probe is withdrawn. Skilled examiners perform observation while inserting the probe.

Figure 11A:
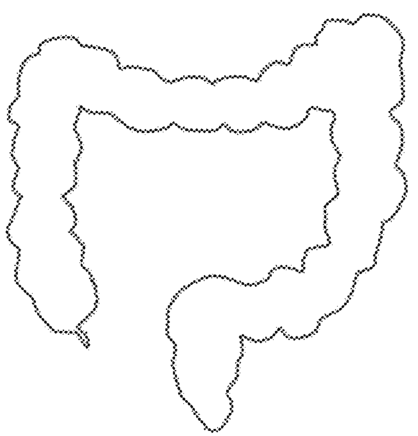
FIGS. 11A, 11B, and 11C are diagrams illustrating examples of displaying the colon.
Figure 11B:
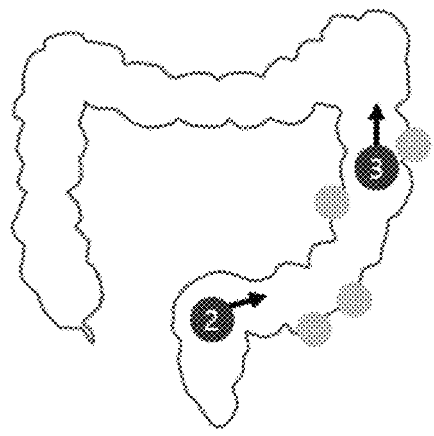
Figure 11C:
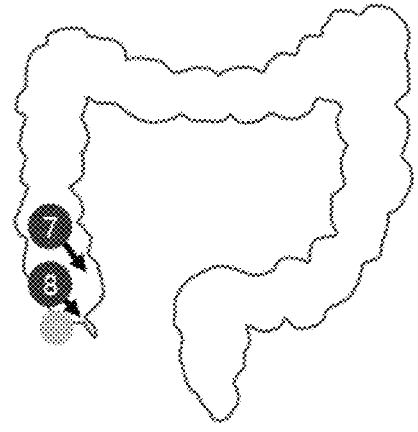

FIGS. 11A, 11B, and 11C are diagrams illustrating examples of displaying the colon.

Referring to FIGS. 11A, 11B, and 11C, FIG. 11A shows the normal colon, FIG. 11B shows the left left-sided colonic diverticulum, and FIG. 11C shows the right-sided colonic diverticulum. The left-sided colonic diverticulum shown in FIG. 11B is mainly formed in the sigmoid colon and the descending colon, and the right-sided colonic diverticulum shown in FIG. 11C is mainly formed in the cecum area.

Herein, the diverticulum as described above is caused by increased pressure within the colon. The diverticula (false diverticula) in the left-sided colon shown in FIG. 11B shows that multiple diverticula are formed in the left-sided colon due to protrusions of parts of the intestinal wall (mucosal and submucosal layer tissues). The false diverticula are acquired rather than congenital and commonly observed in Western populations; however, their incidence has recently increased among Eastern populations as well. The diverticulum (true diverticulum) in the right-sided colon shown in FIG. 11C shows that one diverticulum is formed in the right-sided colon due to a protrusion of all layers of the intestinal wall including the muscular layer. The true diverticula are congenital and commonly found in Eastern populations.

Figure 12:
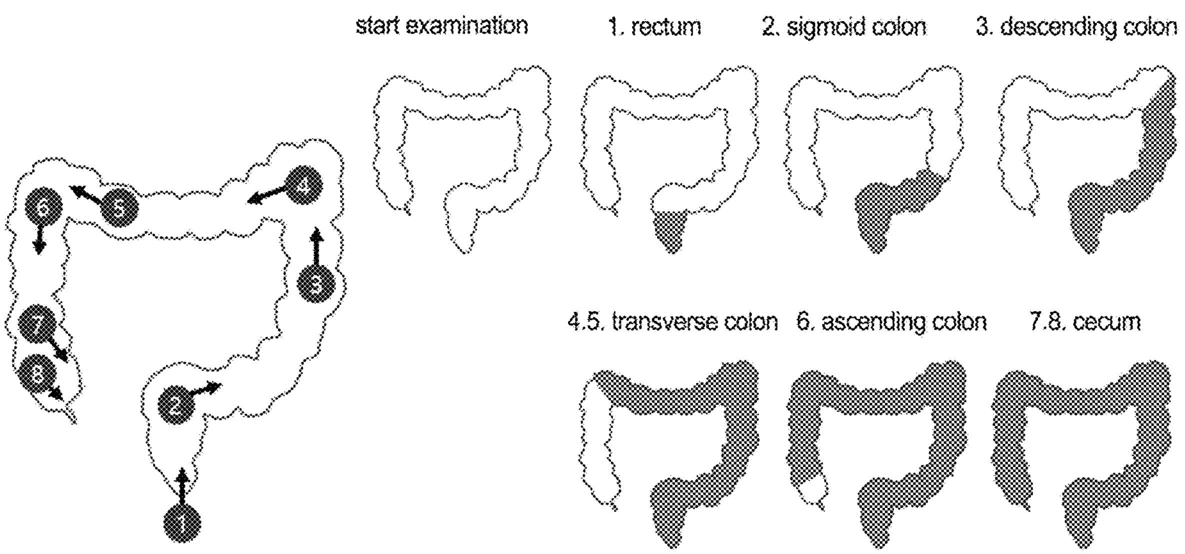
FIG. 12 is a diagram illustrating the display of an examination area of the colon (in the case of the normal colon)

FIG. 12 is a diagram illustrating the display of an examination area of the colon (in the case of the normal colon).

FIG. 12 shows the case of indicating an examination area during a colonoscope probe insertion process. In general, the inside of the colon is observed (examined) in the following order: examination start→rectum observation→sigmoid colon observation→descending colon observation→transverse colon observation→ascending colon observation→cecum observation.

Figure 13:
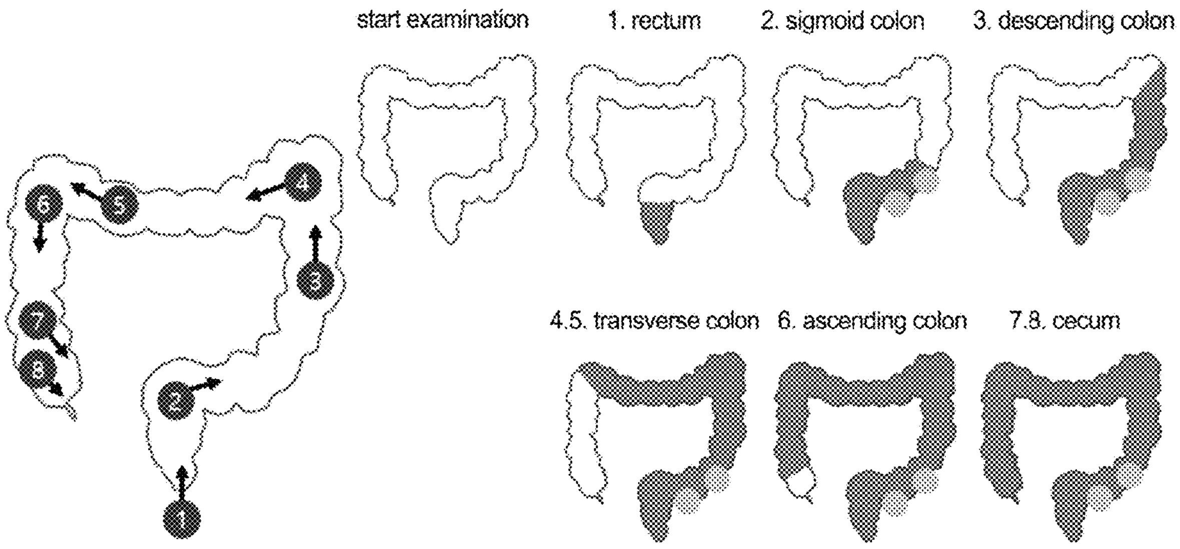
FIG. 13 is a diagram illustrating the display of an examination area of the colon (in the case of a left-sided colonic diverticulum)

FIG. 13 is a diagram illustrating the display of an examination area of the colon (in the case of a left-sided colonic diverticulum).

FIG. 13 shows the case of indicating an examination area during a colonoscope probe insertion process. As in the case of the normal colon shown in FIG. 12, the inside of the colon is observed (examined) in the following order: examination start→rectum observation→sigmoid colon observation→descending colon observation→transverse colon observation-ascending colon observation→cecum observation. This example shows the case in which a diverticulum is found in the sigmoid colon.

Figure 14:
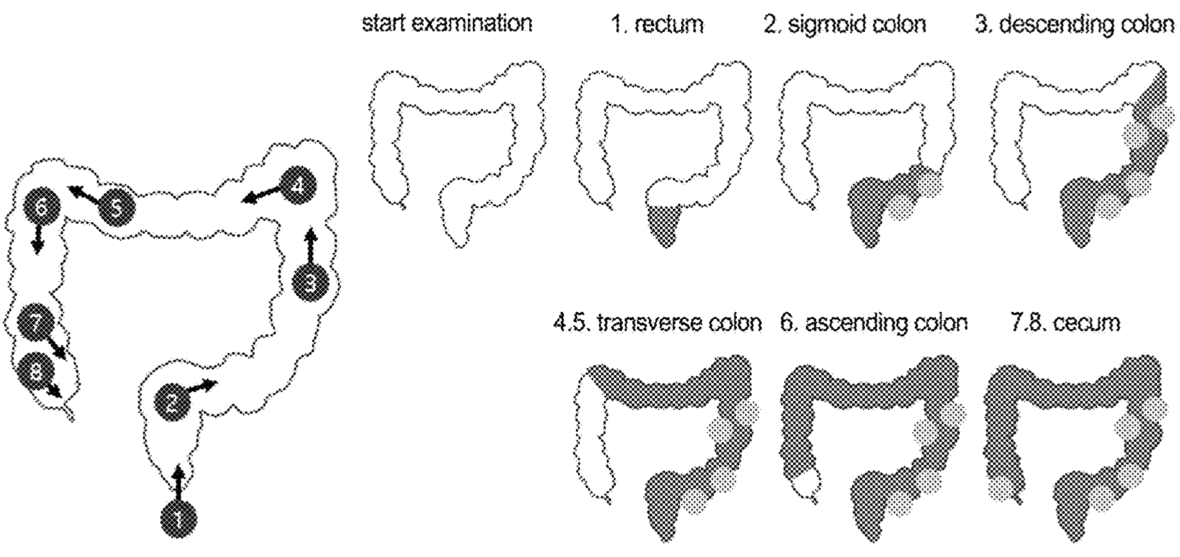
FIG. 14 is a diagram illustrating the display of an examination area of the colon (in the case of left-sided and right-sided colonic diverticula)

FIG. 14 is a diagram illustrating the display of an examination area of the colon (in the case of left-sided and right-sided colonic diverticula).

FIG. 14 shows the case of indicating an examination area during a colonoscope probe insertion process. Similarly, the inside of the colon is observed (examined) in the following order: examination start→rectum observation→sigmoid colon observation→descending colon observation→transverse colon observation→ascending colon observation→cecum observation. This example shows the case in which diverticula are found in the sigmoid colon, the descending colon, and the cecum.

Figure 15:
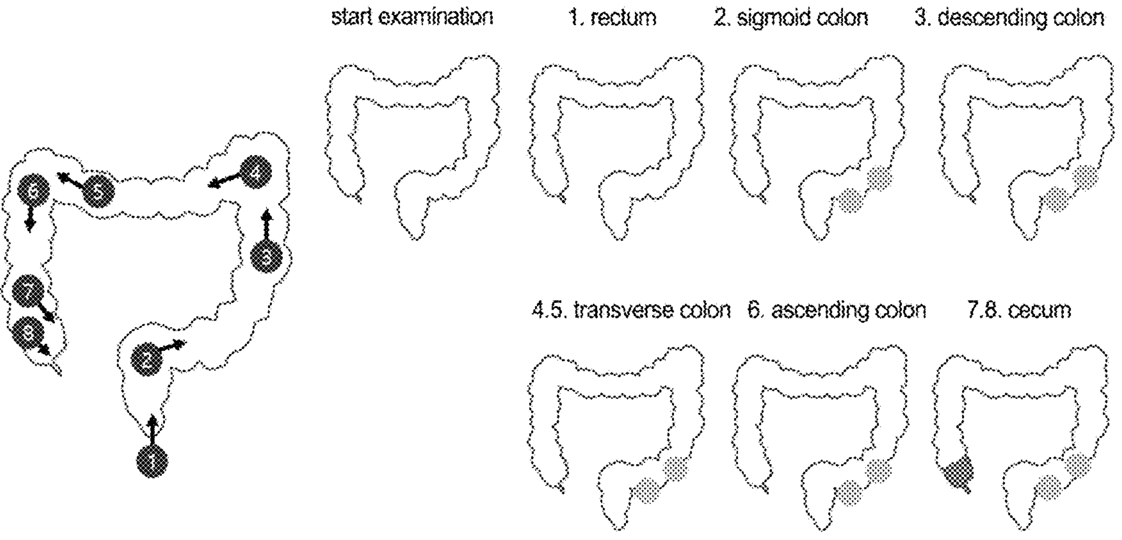
FIG. 15 is a diagram illustrating another example of the display of an examination area of the colon (in the case of a left-sided colonic diverticulum)

FIG. 15 is a diagram illustrating another example of the display of an examination area of the colon (in the case of a left-sided colonic diverticulum).

FIG. 15 shows the case of indicating an examination area during a colonoscope probe insertion process. Similarly, the inside of the colon is observed (examined) in the following order: examination start→rectum observation→sigmoid colon observation→descending colon observation→transverse colon observation→ascending colon observation→cecum observation. This example shows the case in which it is determined only whether insertion into the cecum is made, and a diverticulum is found in the sigmoid colon.

Figure 16:
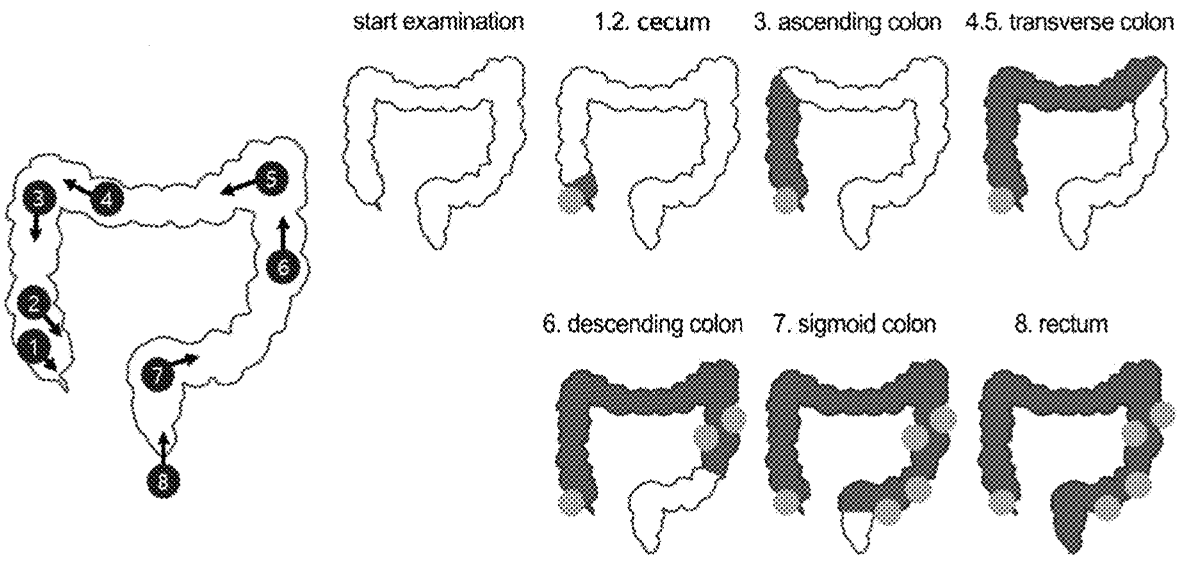
FIG. 16 is a diagram illustrating the display of an examination area of the colon (in the case of right-sided and left-sided colonic diverticula)

FIG. 16 is a diagram illustrating the display of an examination area of the colon (in the case of right-sided and left-sided colonic diverticula).

FIG. 16 shows the case of indicating an examination area during a colonoscope probe withdrawal process. The inside of the colon is observed (examined) in the following order: examination start→cecum observation→ascending colon observation→transverse colon observation→descending colon observation→sigmoid colon observation→rectum observation (that is, in reverse order while the probe is withdrawn).

Figure 17A:
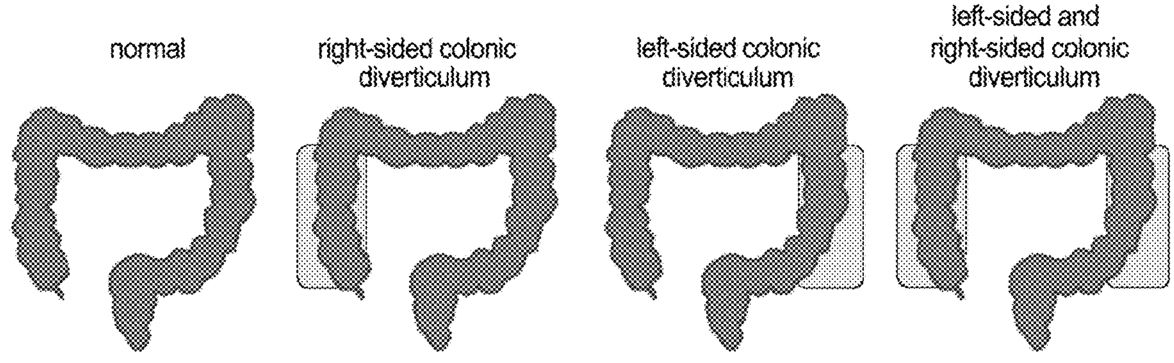
FIGS. 17A and 17B are diagrams illustrating the display of an examination area of the colon (indicating whether a diverticulum is found, distinguishing between a left-sided and a right-sided colonic diverticulum)
Figure 17B:

FIGS. 17A and 17B are diagrams illustrating the display of an examination area of the colon (indicating whether a diverticulum is found, distinguishing between the left-sided and the right-sided colon).

FIGS. 17A and 17B show the case in which whether a diverticulum is found is simply indicated, distinguishing between the left-sided and the right-sided colon. As shown in FIGS. 17A and 17B, in the case of a right-sided colonic diverticulum, a left-sided colonic diverticulum, or both right-sided and left-sided colonic diverticula are found, a particular region area of the left-sided, the right-sided, or the left/right-sided colon is indicated (displayed) so that an examiner visually checks the particular region area. FIG. 17A shows that a main examination area is indicated, and FIG. 17B shows that it is determined whether insertion into the cecum is made.

Figure 18A:
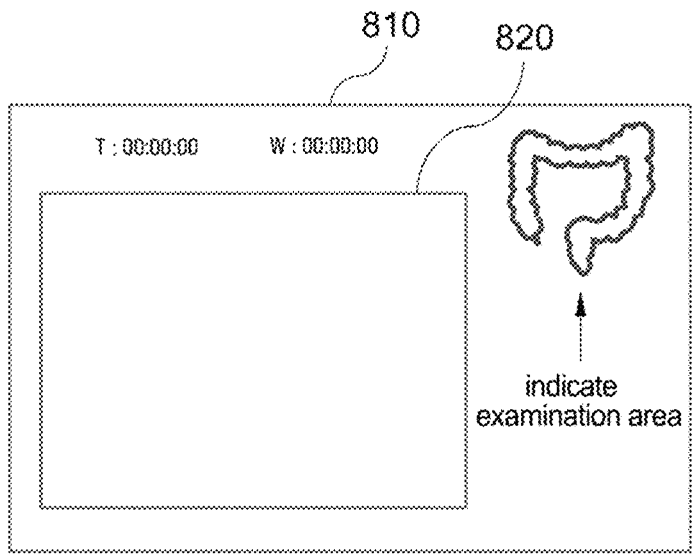
FIGS. 18A, 18B, and 18C are diagrams illustrating examples of providing a result of analysis (an example of an examination of a normal colon)
Figure 18B:
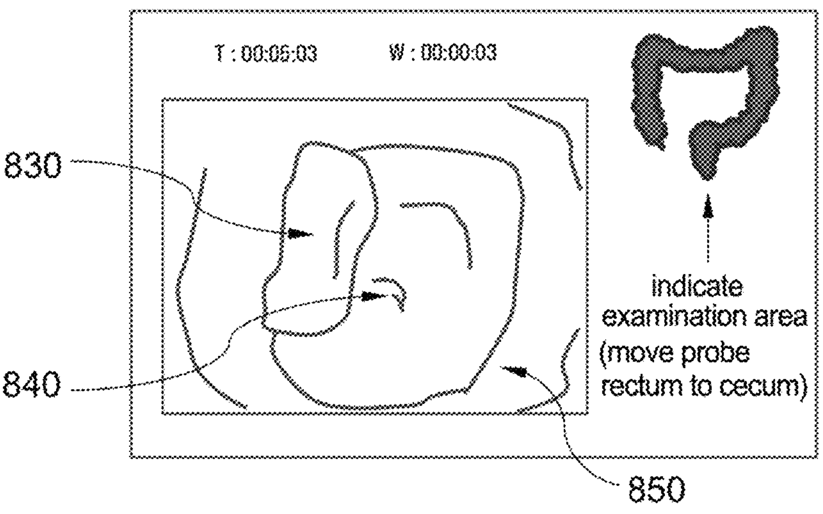
Figure 18C:
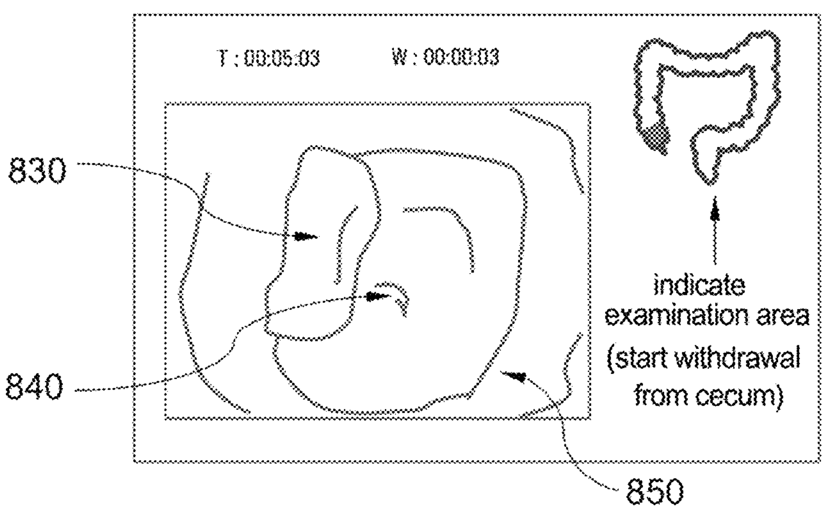

FIGS. 18A, 18B, and 18C are diagrams illustrating examples of providing a result of analysis (an example of an examination of a normal colon).

FIGS. 18A, 18B, and 18C show the provision of a result of analyzing an examination of a normal colon. FIG. 18A shows a colonoscopy start screen, FIG. 18B shows a screen displaying an example of the cecum examination during the probe insertion process, and FIG. 18C shows a screen displaying an example of the cecum examination during the probe withdrawal process. In FIGS. 18A, 18B, and 18C, reference numeral 810 denotes a colonoscopy image analysis software screen, 820 denotes a colonoscopy image analysis region, 830 denotes the ileocecal valve, 840 denotes the appendix, and 850 denotes the cecum. In addition, T denotes the examination time, and W denotes the withdrawal time.

Figure 19A:
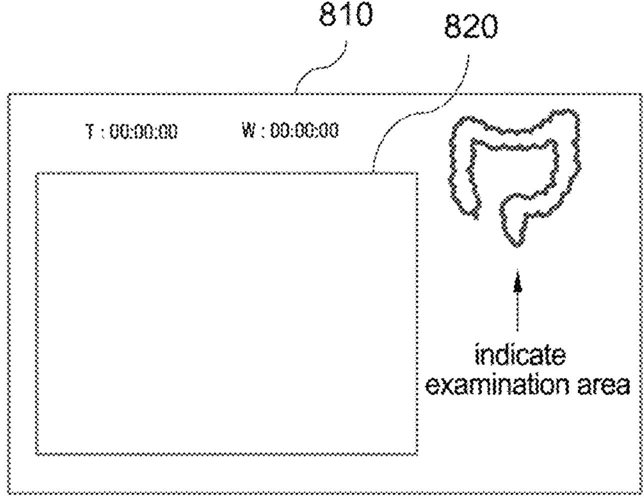
FIGS. 19A, 19B, and 19C are diagrams illustrating examples of providing a result of analysis (examples of finding a diverticulum in the cecum)
Figure 19B:
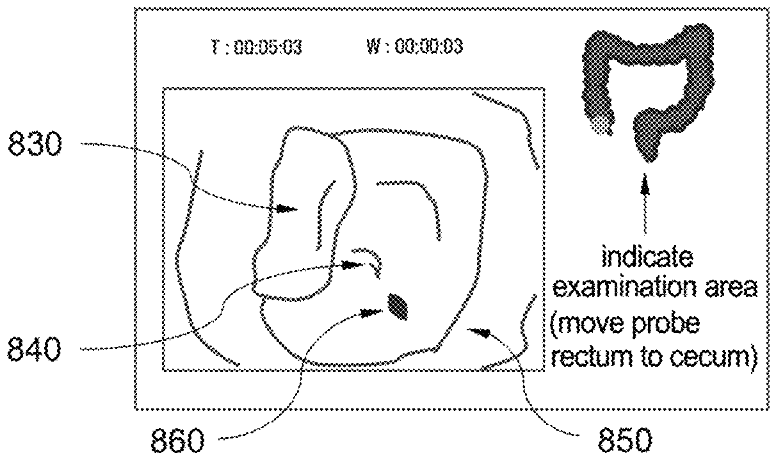
Figure 19C:
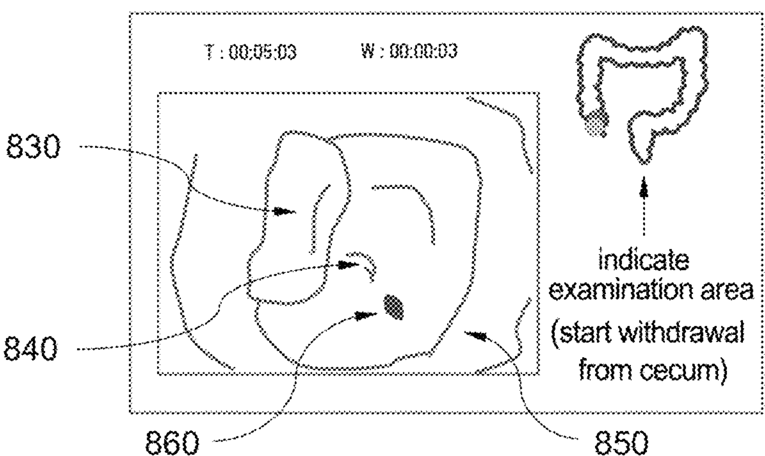

FIGS. 19A, 19B, and 19C are diagrams illustrating examples of providing a result of analysis (examples of finding a diverticulum in the cecum).

FIGS. 19A, 19B, and 19C show the provision of a result of analysis of the detection of a diverticulum in the cecum. Similarly, FIG. 19A shows a colonoscopy start screen, FIG. 19B shows a screen displaying an example of the cecum examination during the probe insertion process, and FIG. 19C shows a screen displaying an example of the cecum examination during the probe withdrawal process. In FIGS. 19A, 19B, and 19C, reference numeral 810 denotes a colonoscopy image analysis software screen, 820 denotes a colonoscopy image analysis region, 830 denotes the ileocecal valve, 840 denotes the appendix, 850 denotes the cecum, and 860 denotes the diverticulum. In addition, T denotes the examination time, and W denotes the withdrawal time.

Figure 20A:
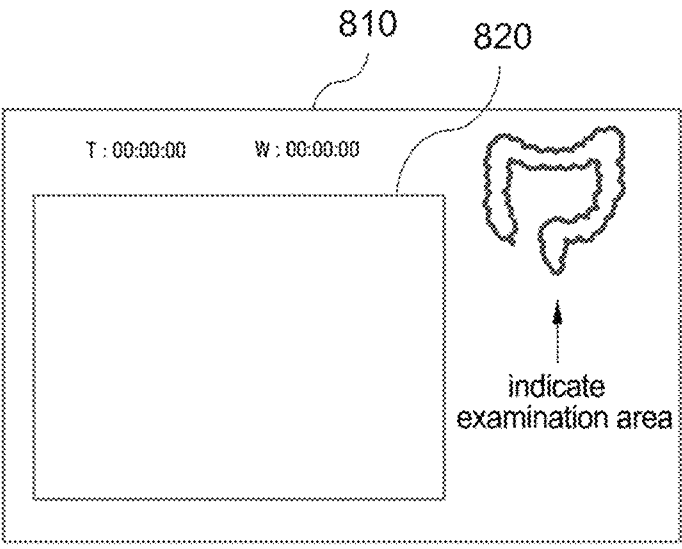
FIGS. 20A, 20B, and 20C are diagrams illustrating examples of providing a result of analysis (examples of finding a diverticulum in the sigmoid colon.
Figure 20B:
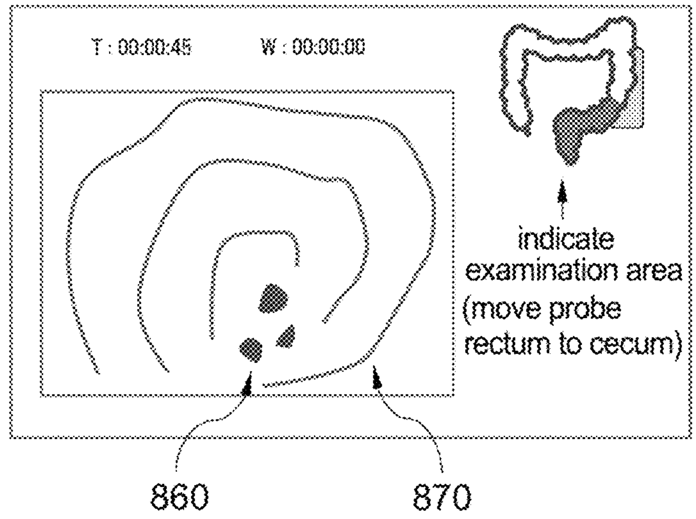
Figure 20C:
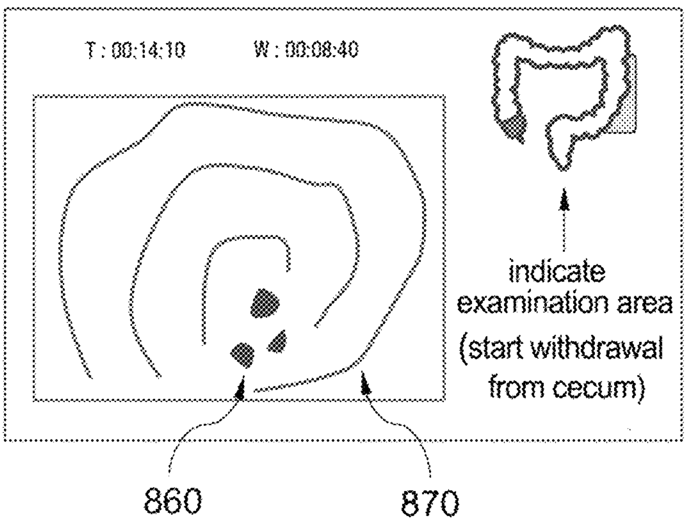

FIGS. 20A, 20B, 20C are diagrams illustrating examples of providing a result of analysis (examples of finding a diverticulum in the sigmoid colon).

FIGS. 20A, 20B, and 20C show the provision of a result of analysis of the detection of a diverticulum in the sigmoid colon. Similarly, FIG. 20A shows a colonoscopy start screen, FIG. 20B shows a screen displaying an example of the sigmoid colon examination during the probe insertion process, and FIG. 20C shows a screen displaying an example of the sigmoid colon examination during the probe withdrawal process. In FIGS. 20A, 20B, and 20C, reference numeral 810 denotes a colonoscopy image analysis software screen, 860 denotes a diverticulum, and 870 denotes the sigmoid colon. In addition, T denotes the examination time, and W denotes the withdrawal time.

FIGS. 21A, 21B, 21C, and 21D are diagrams illustrating examples of providing a result of analysis (examples of result reports).

Figure 21A:
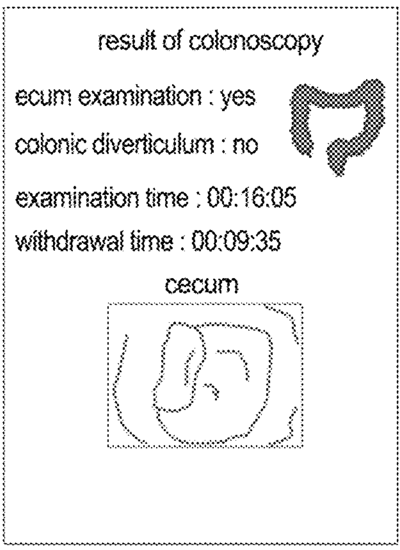
FIGS. 21A, 21B, 21C, and 21D are diagrams illustrating examples of providing a result of analysis (examples of result reports).
Figure 21B:
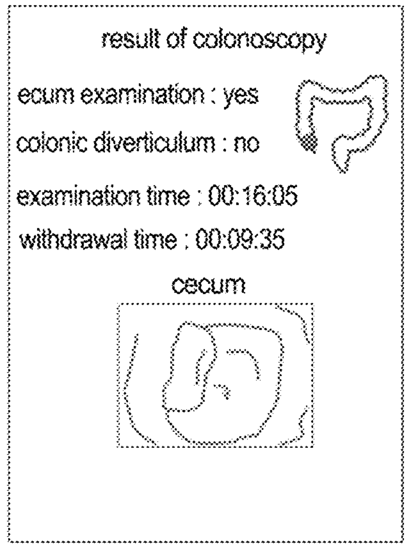
Figure 21C:
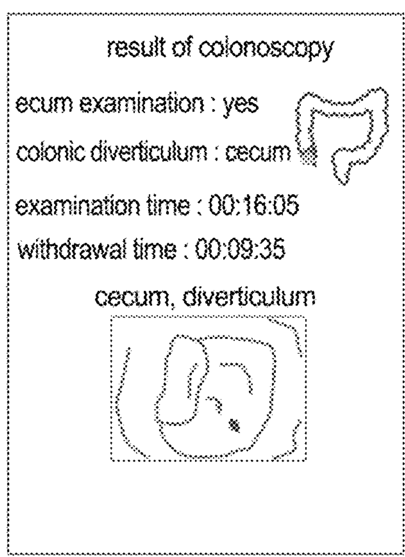
Figure 21D:
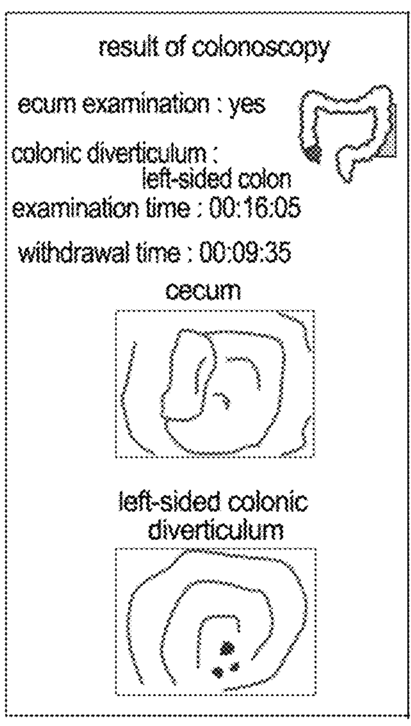

Referring to FIGS. 21A, 21B, 21C, and 21D, a result of colonoscopy is shown. FIG. 21A shows indication of an examination area starting from probe insertion, and this is the case in which a cecum examination is performed and there is no colonic diverticulum. FIG. 21B shows indication of whether a cecum examination is performed, and this is the case in which a cecum examination is performed and there is no colonic diverticulum. FIG. 21C shows indication of whether a cecum examination is performed and indication of a diverticulum, and this is the case in which a cecum examination is performed and there is a colonic diverticulum in the cecum. FIG. 21D shows indication of whether a cecum examination is performed and simple indication of a left-sided colonic diverticulum, and this is the case in which a cecum examination is performed and there is a colonic diverticulum in the left-sided colon.

As described above, the colonoscopy area indication system and method according to the present disclosure can inform the examiner of conditions, such as a diverticulum protruding from the colon wall, or can indicate (display) a diverticulum on the examination screen differently from a normal colon, in indicating the main examination area by applying the image recognition technology to the colonoscopy process. Accordingly, the colonoscopy area indication system and method enable the examiner to conduct the examination with caution against complications, such as perforations, assist in setting a probe movement path, and allow the examiner to perform a more thorough colonoscopy.

In addition, the colonoscopy area indication system and method indicate the main colon examination area to enable the examiner to identify the area examined so far, and report whether a cecum examination is performed to use this as an indicator of the quality of colonoscopy, and record whether there is a diverticulum so that the examiner is aware of the risk of perforations in advance when conducting a subsequent colonoscopy.

Although an exemplary embodiment of the present disclosure has been described in detail, the present disclosure is not limited thereto, and it is obvious to those skilled in the art that various modification and applications can be made within the scope of the technical idea of the present disclosure. Accordingly, the true scope of the present disclosure should be interpreted by the following claims, and all technical ideas within the scope equivalent thereto should be interpreted as being included in the scope of the present disclosure.

What is claimed is:

1. A colonoscopy area indication system, comprising:

a model loading/condition setting part that loads a colonoscopy image analysis model, and set an analysis condition of the analysis model;

an image receiving part that receives a colonoscopy image frame;

an image preprocessing part that preprocesses a colonoscopy image received through the image receiving part, and makes a resultant preprocessed colonoscopy image ready for smooth subsequent image analysis;

an image analysis part that analyzes the colonoscopy image preprocessed by the image preprocessing part by using the image analysis model based on artificial intelligence (AI), and detects and indicates, on the basis of a result of analysis, at least one selected from a group of an examination area, a diverticulum area, and a lesion area in the colonoscopy image; and a controller that checks states and controls operations of the model loading/condition setting part, the image receiving part, the image preprocessing part, and the image analysis part, and initializes an analysis screen and displays a picture of a normal colon when the model loading/condition setting part completes loading of the colonoscopy image analysis model and setting of the analysis condition of the analysis model, and provides the result of analysis performed by the image analysis part, wherein detecting and indicating at least one selected from the group of the examination area, the diverticulum area, and the lesion area in the colonoscopy image by the image analysis part comprises the controller transmitting, to the image analysis part, an indication condition change command based on a detection state of the diverticulum area, the command suppressing the indication of a diverticulum when the colonoscopy image corresponds to a normal colon and enabling diverticulum indication when a diverticulum is detected, and further indicating examination time and withdrawal time.

2. The colonoscopy area indication system of claim 1, wherein preprocessing of the colonoscopy image by the image preprocessing part includes analysis region cropping and input size adjustment.

3. The colonoscopy area indication system of claim 1, wherein the image analysis model of the image analysis part is configured as a single image analysis model for detecting the examination area and the diverticulum area.

4. The colonoscopy area indication system of claim 1, wherein the image analysis model of the image analysis part is configured to include an examination area detection model for detecting the examination area, and a diverticulum detection model for detecting the diverticulum area.

5. The colonoscopy area indication system of claim 1, wherein the image analysis model of the image analysis part is configured to include an examination area detection model for detecting the examination area, a diverticulum detection model for detecting the diverticulum area, and a lesion detection model for detecting the lesion area.

6. The colonoscopy area indication system of claim 1, wherein the image analysis model of the image analysis part is configured to include a cecum/diverticulum detection model for detecting a cecum and a diverticulum, and a lesion detection model for detecting the lesion area.

7. The colonoscopy area indication system of claim 6, wherein the lesion detection model has a lesion attribute identification function for determining whether a lesion is benign or malignant.

8. The colonoscopy area indication system of claim 1, wherein in detecting and indicating at least one selected from the group of the examination area, the diverticulum area, and the lesion area in the colonoscopy image by the image analysis part, the examination area includes an appendix, a cecum, an ascending colon, a transverse colon, a descending colon, a sigmoid colon, and a rectum.

9. A colonoscopy area indication system, comprising:

a model loading/condition setting part that loads a colonoscopy image analysis model and a speech keyword recognition model, and set an analysis condition of the analysis model;

an image receiving part that receives a colonoscopy image frame;

an image preprocessing part that preprocesses a colonoscopy image received through the image receiving part, and makes a resultant preprocessed colonoscopy image ready for smooth subsequent image analysis is smoothly performed;

an image analysis part that analyzes the colonoscopy image preprocessed by the image preprocessing part by using the image analysis model based on artificial intelligence (AI), and detects and indicates, on the basis of a result of analysis, at least one selected from a group of an examination area, a diverticulum area, and a lesion area in the colonoscopy image;

a speech recognition part that reads audio from a buffer storing the audio while the image analysis part performs the image analysis, and analyzes the audio using the speech keyword recognition model based on AI, and recognizes a speech keyword on the basis of the result of analysis and transmits the speech keyword to the image analysis part; and a controller that checks states and control operations of the model loading/condition setting part, the image receiving part, the image preprocessing part, the image analysis part, and the speech recognition part, and initializes an analysis screen and displays a picture of a normal colon when the model loading/condition setting part completes loading of the colonoscopy image analysis model and setting of the analysis condition of the analysis model, and provides the result of analysis performed by the image analysis part, wherein the result of analysis is provided by linking an analysis target detected by the image analysis model with a speech command (keyword) related to the analysis target spoken by an examiner, wherein detecting and indicating at least one selected from the group of the examination area, the diverticulum area, and the lesion area in the colonoscopy image by the image analysis part comprises the controller transmitting, to the image analysis part, an indication condition change command based on a detection state of the diverticulum area, the command suppressing the indication of a diverticulum when the colonoscopy image corresponds to a normal colon and enabling diverticulum indication when a diverticulum is detected, and further indicating examination time and withdrawal time, wherein the speech recognition part continuously analyzes buffered audio in parallel with the image analysis and the controller links a recognized speech keyword to a corresponding analysis target only when both occur within a common temporal window.

10. The colonoscopy area indication system of claim 9, wherein preprocessing of the colonoscopy image by the image preprocessing part includes analysis region cropping and input size adjustment.

11. The colonoscopy area indication system of claim 9, wherein the image analysis model of the image analysis part is configured as a single image analysis model for detecting the examination area and the diverticulum area.

12. The colonoscopy area indication system of claim 9, wherein the image analysis model of the image analysis part is configured to include an examination area detection model for detecting the examination area, and a diverticulum detection model for detecting the diverticulum area.

13. The colonoscopy area indication system of claim 9, wherein the image analysis model of the image analysis part is configured to include an examination area detection model for detecting the examination area, a diverticulum detection model for detecting the diverticulum area, and a lesion detection model for detecting the lesion area.

14. The colonoscopy area indication system of claim 9, wherein the image analysis model of the image analysis part is configured to include a cecum/diverticulum detection model for detecting a cecum and a diverticulum, and a lesion detection model for detecting the lesion area.

15. The colonoscopy area indication system of claim 14, wherein the lesion detection model has a lesion attribute identification function for determining whether a lesion is benign or malignant.

16. The colonoscopy area indication system of claim 9, wherein in detecting and indicating at least one selected from the group of the examination area, the diverticulum area, and the lesion area in the colonoscopy image by the image analysis part, the examination area includes an appendix, a cecum, an ascending colon, a transverse colon, a descending colon, a sigmoid colon, and a rectum.

* * * * *